United States Patent
Steynberg et al.

(10) Patent No.: US 9,950,975 B2
(45) Date of Patent: *Apr. 24, 2018

(54) PROCESS FOR OPERATING AN INTEGRATED GAS-TO-LIQUIDS FACILITY

(71) Applicant: Velocys Technologies, Ltd., Abingdon (GB)

(72) Inventors: Andre Steynberg, Dublin, OH (US); Roy Lipski, Plain City, OH (US)

(73) Assignee: VELOCYS TECHNOLOGIES, LTD., Abingdon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/664,078

(22) Filed: Jul. 31, 2017

(65) Prior Publication Data

US 2017/0327444 A1 Nov. 16, 2017

Related U.S. Application Data

(63) Continuation of application No. 15/141,685, filed on Apr. 28, 2016, now Pat. No. 9,725,385.

(Continued)

(51) Int. Cl.
*C01B 13/02* (2006.01)
*C01B 3/48* (2006.01)
(Continued)

(52) U.S. Cl.
CPC ......... *C07C 29/1518* (2013.01); *C01B 3/382* (2013.01); *C01B 3/48* (2013.01);
(Continued)

(58) Field of Classification Search
CPC ..... C07C 29/1518; C07C 27/06; C01B 3/382; C01B 3/48; C01B 2203/1241; C01B 2203/0238; C10G 2/32
See application file for complete search history.

(56) References Cited

U.S. PATENT DOCUMENTS 4,791,079 A 12/1988 Hazbun
5,597,773 A 1/1997 Evans et al.
(Continued)

FOREIGN PATENT DOCUMENTS

EP 0 266 015 A1 5/1988
EP 2 367 756 A2 9/2011
(Continued)

OTHER PUBLICATIONS

International Search Report & Written Opinion in International Application No. PCT/US2016/029873, dated Jul. 27, 2016 (16 pages).

(Continued)

*Primary Examiner* — Jafar Parsa
(74) *Attorney, Agent, or Firm* — Foley & Lardner LLP

(57) ABSTRACT

The present technology is directed to processes involving formation of hydrocarbons and oxygenated hydrocarbons through use of oxygen supplied by ion transport membranes. More particularly, the present technology relates in part to a process involving steam reforming and subsequent production of a synthetic product where carbon dioxide and/or hydrogen downstream of the process is reclaimed to generate the synthetic product. The present technology also relates in part to an ethylene formation process involving a viral-templated coupling catalyst in the presence of an ion transport membrane.

20 Claims, 3 Drawing Sheets

Related U.S. Application Data

(60) Provisional application No. 62/155,995, filed on May 1, 2015.

(51) Int. Cl.
| | |
|---|---|
| *C01B 3/38* | (2006.01) |
| *C07C 29/151* | (2006.01) |
| *C07C 2/84* | (2006.01) |
| *C07C 27/06* | (2006.01) |
| *C10G 2/00* | (2006.01) |

(52) U.S. Cl.
CPC ............ *C01B 13/0251* (2013.01); *C07C 2/84* (2013.01); *C07C 27/06* (2013.01); *C10G 2/00* (2013.01); *C01B 2203/025* (2013.01); *C01B 2203/0233* (2013.01); *C01B 2203/0238* (2013.01); *C01B 2203/0244* (2013.01); *C01B 2203/0283* (2013.01); *C01B 2203/043* (2013.01); *C01B 2203/0405* (2013.01); *C01B 2203/0415* (2013.01); *C01B 2203/061* (2013.01); *C01B 2203/062* (2013.01); *C01B 2203/0822* (2013.01); *C01B 2203/1241* (2013.01); *Y02P 20/128* (2015.11)

(56) References Cited

U.S. PATENT DOCUMENTS

| | | | |
|---|---|---|---|
| 5,703,253 | A | 12/1997 | Evans et al. |
| 5,705,661 | A | 1/1998 | Iwakura et al. |
| 6,010,614 | A | 1/2000 | Keskar et al. |
| 6,296,686 | B1 | 10/2001 | Prasad et al. |
| 6,312,586 | B1 | 11/2001 | Kalnes et al. |
| 6,762,311 | B2 | 7/2004 | Rizkalla et al. |
| 7,014,835 | B2 | 3/2006 | Mathias et al. |
| 7,673,857 | B2 | 3/2010 | White et al. |
| 7,686,856 | B2 | 3/2010 | Hemmings et al. |
| 7,690,204 | B2 | 4/2010 | Drnevich et al. |
| 7,754,067 | B2 | 7/2010 | Allam |
| 7,820,033 | B2 | 10/2010 | Eng et al. |
| 7,858,667 | B2 | 12/2010 | Hu et al. |
| 8,007,761 | B2 | 8/2011 | Drnevich et al. |
| 8,152,898 | B2 | 4/2012 | Prasad et al. |
| 8,206,669 | B2 | 6/2012 | Schaffer et al. |
| 8,226,912 | B2 | 7/2012 | Kloosterman et al. |
| 8,262,755 | B2 | 9/2012 | Repasky et al. |
| 8,287,762 | B2 | 10/2012 | Repasky et al. |
| 8,349,214 | B1 | 1/2013 | Kelly et al. |
| 8,419,827 | B2 | 4/2013 | Repasky et al. |
| 8,431,506 | B2 | 4/2013 | Neltner et al. |
| 8,436,506 | B2 | 5/2013 | Wang et al. |
| 8,518,356 | B2 | 8/2013 | Schaffer et al. |
| 8,591,718 | B2 | 11/2013 | Lane et al. |
| 8,592,492 | B2 | 11/2013 | Chakravarti et al. |
| 8,623,241 | B2 | 1/2014 | Kelly et al. |
| 8,728,202 | B2 | 5/2014 | Repasky et al. |
| 2010/0189610 | A1 | 7/2010 | Allam |
| 2011/0240924 | A1 | 10/2011 | Repasky |
| 2012/0014851 | A1 | 1/2012 | Kloosterman et al. |
| 2012/0027655 | A1 | 2/2012 | Schaffer et al. |
| 2012/0027656 | A1 | 2/2012 | Schaffer et al. |
| 2012/0041246 | A1 | 2/2012 | Scher et al. |
| 2012/0128560 | A1 | 5/2012 | Krishnamurthy et al. |
| 2012/0286210 | A1 | 11/2012 | Krishnamurthy et al. |
| 2013/0043432 | A1 | 2/2013 | Repasky et al. |
| 2013/0062567 | A1 | 3/2013 | Repasky et al. |
| 2013/0315794 | A1 | 11/2013 | Schaffer et al. |
| 2014/0048126 | A1 | 2/2014 | Dorval Courchesne et al. |
| 2014/0077133 | A1 | 3/2014 | Krishnamurthy et al. |
| 2014/0121433 | A1 | 5/2014 | Cizeron et al. |
| 2014/0175335 | A1 | 6/2014 | Anderson et al. |
| 2015/0152025 | A1 | 6/2015 | Cizeron et al. |

FOREIGN PATENT DOCUMENTS

| | | | |
|---|---|---|---|
| EP | 2 374 534 | A1 | 10/2011 |
| EP | 2 407 229 | A1 | 1/2012 |
| EP | 2 412 667 | A1 | 2/2012 |
| EP | 2 412 668 | A1 | 2/2012 |
| EP | 2 537 580 | A1 | 12/2012 |
| EP | 0 926 097 | B2 | 2/2013 |
| EP | 1 838 611 | B1 | 9/2013 |
| EP | 2 746 368 | A1 | 6/2014 |
| EP | 1 690 826 | B1 | 8/2014 |
| WO | WO-2004/016347 | A2 | 2/2004 |
| WO | WO-2008/150451 | A2 | 12/2008 |
| WO | WO-2010/047942 | A2 | 4/2010 |
| WO | WO-2010/075591 | A2 | 7/2010 |
| WO | WO-2011/112484 | A1 | 9/2011 |
| WO | WO-2011/133264 | A1 | 10/2011 |
| WO | WO-2011/149914 | A1 | 12/2011 |
| WO | WO-2012/054455 | A2 | 4/2012 |
| WO | WO-2012/064936 | A1 | 5/2012 |
| WO | WO-2012/158536 | A1 | 11/2012 |
| WO | WO-2013/009559 | A1 | 1/2013 |
| WO | WO-2013/009560 | A1 | 1/2013 |
| WO | WO-2014/026204 | A1 | 2/2014 |
| WO | WO-2014/077975 | A2 | 5/2014 |
| WO | WO-2014/085109 | A1 | 6/2014 |
| WO | WO-2014/209605 | A1 | 12/2014 |

OTHER PUBLICATIONS

Li, D. et al., "The performances of higher alcohol synthesis over nickel modified $K_2CO_3/MoS_2$ catalyst," Fuel Processing Technology, 2007, 88, 125-127.

Non-Final Office Action in U.S. Appl. No. 15/141,685, dated Mar. 10, 2017 (6 pages).

Notice of Allowance in U.S. Appl. No. 15/141,685, dated Apr. 7, 2017 (7 pages).

Xiang, M. et al., "Synthesis of higher alcohols from syngas over Fischer-Tropsch elements modified K/β—Mo2C catalysts," Fuel, 2008, 87, pp. 599-603.

Xiang, M. et al., "Synthesis of higher alcohols from syngas over K/Co/β—Mo2C catalysts," Catalysis Communications, 2007, 8, pp. 503-507.

PROCESS FOR OPERATING AN INTEGRATED GAS-TO-LIQUIDS FACILITY

CROSS-REFERENCE TO RELATED APPLICATIONS

This application is a continuation of U.S. application Ser. No. 15/141,685, filed on Apr. 28, 2016, which claims priority to U.S. Provisional Application No. 62/155,995, filed on May 1, 2015. The contents of each are incorporated by reference in their entirety for any and all purposes.

FIELD

The present technology relates to reforming and synthesis processes for use in an integrated gas-to-liquids facility. More particularly it relates in part to a process involving steam reforming and subsequent production of a synthetic product where carbon dioxide and/or hydrogen downstream of the process is reclaimed to generate the synthetic product. The present technology also relates in part to an ethylene formation process involving a viral-templated coupling catalyst in the presence of an ion transport membrane.

SUMMARY

The present technology provides processes that not only manage $CO_2$ downstream of reforming and/or synthetic processes but also uses this $CO_2$ as a resource to advantageously produce useful products and/or facilitate other processes. $H_2$ from downstream of reforming and/or synthetic processes may also be reclaimed. In addition, the present technology optionally provides for the use of $H_2O$ downstream of a reforming process and/or $H_2O$ downstream of a synthetic reaction to facilitate production of useful products in the presently disclosed process.

In one aspect, the present technology provides a steam reforming process that involves steam reforming a first reforming feed to produce a steam reformed product that includes $H_2$ and CO; optionally subjecting a second reforming feed that includes the steam reformed product to a second reforming step to provide a second reformed product that includes $H_2$ and CO; and contacting the $H_2$ and CO with a synthesis catalyst to produce a synthetic product and a tail gas. The synthetic product includes one or more compounds selected from $C_1$ to $C_{100}$ hydrocarbons, $C_1$ to $C_{100}$ oxygenated hydrocarbons, or a combination thereof; the tail gas includes $CO_2$. In the present steam reforming process, heat for the steam reforming step is provided by combustion. Such combustion involves flowing a combustion gas (which includes $H_2$) over a permeate surface of an ion transport membrane and flowing an $O_2$-containing gas over a retentate surface of an ion transport membrane to react the combustion gas, produce heat, and produce an exhaust gas.

Notably, in the steam reforming process, the first reforming feed includes $CH_4$ and the first and/or the second reforming feed includes one or more of
  (1) $CO_2$ separated from the steam reformed product and/or the second reformed product,
  (2) $CO_2$ separated from the tail gas, or
  (3) $CO_2$ formed from subjecting at least a portion of the tail gas to a water-gas shift ("WGS") reaction which forms a WGS product that includes the $CO_2$ and H2.

In a related aspect, the present technology involves forming ethylene by flowing a reactant feed (which includes methane) over a viral-templated coupling catalyst disposed on a permeate side of an ion transport membrane and flowing an $O_2$-containing gas over a retentate side of the ion transport membrane, where flowing the $O_2$-containing gas over the retentate side of the ion transport membrane produces an $O_2$-depleted gas. In any of the embodiments of such a process, it may be the process produces an ethylene formation product that includes ethylene. In such embodiments, the ethylene formation product may be separated to provide ethylene and an ethylene formation tail gas ("EF tail gas"). The EF tail gas may be directed to the WGS reaction of the steam reforming process of the present technology. In any of the embodiments of the process involving forming ethylene, it may be that forming ethylene provides heat to the steam reforming step of the steam reforming process of the present technology.

BRIEF DESCRIPTION OF THE DRAWINGS

In FIG. 1, the combustion chamber exhaust gas includes $CO_2$ from downstream of the steam reforming step which serves to increase the ratio of carbon monoxide relative to hydrogen in the feed to the conversion process.

In FIG. 2, the autothermal reformer provides a syngas product and heat for the prior steam reforming step, according to several embodiments.

DETAILED DESCRIPTION

I. Definitions

Figure 1:
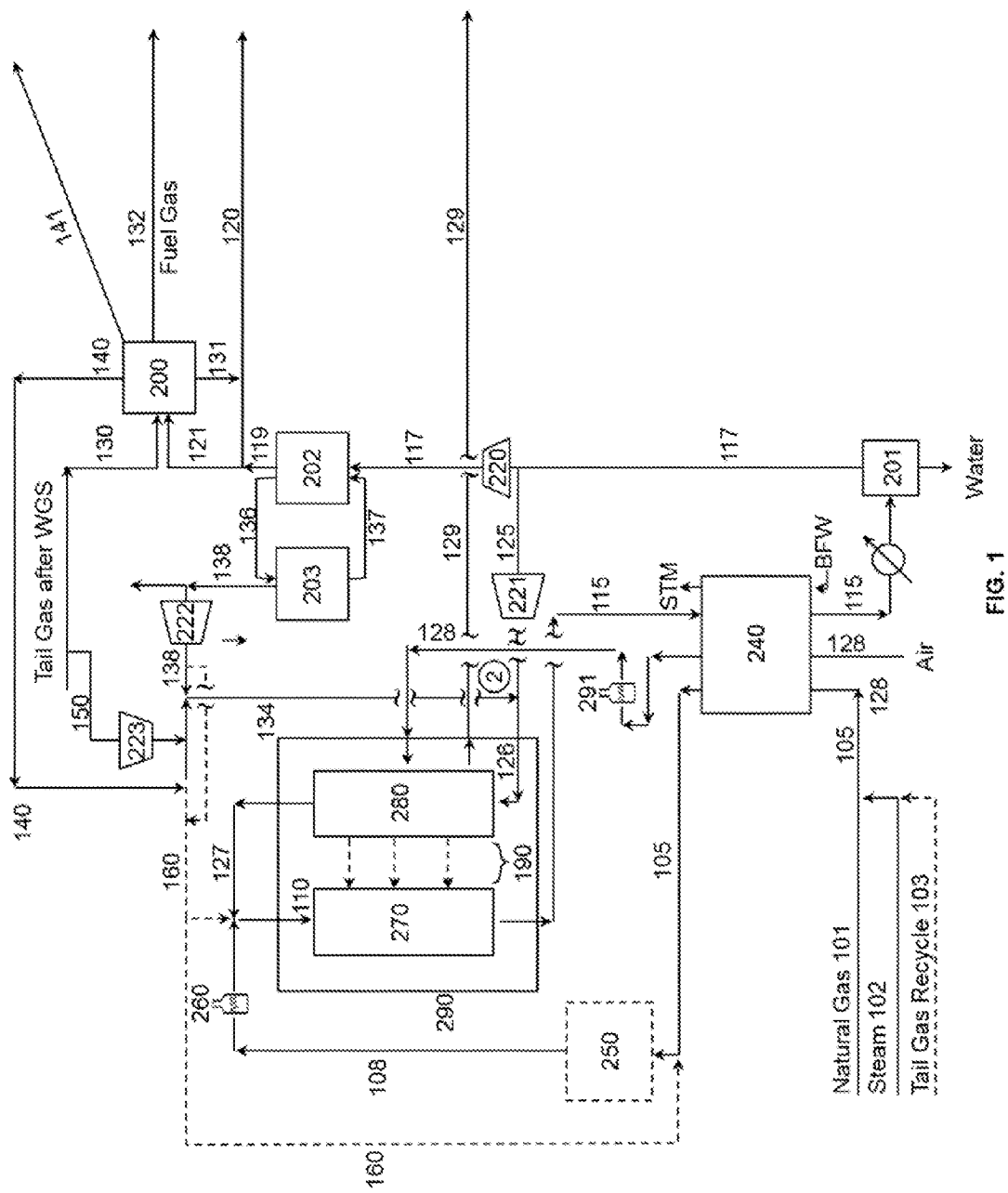
FIG. 1 illustrates a process involving steam reforming where the steam reforming feed includes an exhaust gas from a combustion chamber and the combustion chamber utilizes an ion transport membrane to provide the oxygen used in the combustion, according to several embodiments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

The term "microchannel" as used herein refers to a channel having at least one internal dimension of height or width of up to about 10 millimeters (mm). The internal dimension of height or width, may be in the range from about 0.05 mm to about 10 mm, or from about 0.05 mm to 5 mm, or from about 0.05 mm to about 2 mm, or from about 0.1 mm to about 2 mm, or from about 0.5 mm to about 2 mm, or from about 0.5 mm to about 1.5 mm, or from about 0.08 mm to about 1.2 mm. The other internal dimension of height or width may be of any dimension, for example, up to about 10 centimeters (cm), or from about 0.1 cm to about 10 cm, or from about 0.5 cm to about 10 cm, or from about 0.5 cm to about 5 cm. The microchannel may include at least one inlet and at least one outlet wherein the at least one inlet is distinct from the at least one outlet. In any of the above embodiments, it may be the microchannel has a length up to about 10 meters. It may be the length of the microchannel up to about 250 cm, or from about 5 cm to about 250 cm, or from about 10 cm to about 100 cm, or from about 10 cm to about 75 cm, or from about 10 cm to about 60 cm. It may be that the length of the microchannel may be at least about two times the height or width. In any of the above embodiments, it may be the microchannel has a length at least about five times the height or width, or at least about ten times the height or width. The microchannel may have a cross section having any shape, for example, a square, rectangle, circle, semi-circle, or trapezoid. The shape and/or size of the cross section of the microchannel may vary over its length. For example, the height or width may taper from a relatively large dimension to a relatively small dimension, or vice versa, over the length of the microchannel.

A "portion" of a composition or stream, as used herein, means from about 1% to about 100% by volume of the composition or stream, or any range including or in between any two integers from about 1% to about 100%.

A "pre-reformer" as used herein will readily be understood by persons of ordinary skill in the art as distinguishable from a steam reformer. Typically, a pre-reformer houses the adiabatic reaction of a hot feed with steam and optionally carbon dioxide. A pre-reformer is not to be confused with a steam reformer, where operation of a steam reformer is typically characterized by heat input to the reaction zone and is described more fully herein.

"Substantially free" as used herein will be understood by persons of ordinary skill in the art and will vary to some extent depending upon the context. If there are uses of the term which are not clear to persons of ordinary skill in the art, given the context in which it is used, "substantially free" will mean less than about 0.5% of the composition on a molar basis.

The term "synthetic product" as used herein in regard to the presently disclosed technology includes hydrocarbons, oxygenated hydrocarbons, or combinations thereof. Oxygenated hydrocarbons include, but are not limited to, alkanes, alkenes, and alkynes that are each substituted with one or more of an epoxy, hydroxyl, or a carbonyl group. Exemplary carbonyl-containing groups include, but are not limited to an aldehyde, a ketone, a carboxylic acid, a carboxylic acid anhydride, or an ester. Thus, the synthetic product of the present technology includes one or more compounds selected from $C_1$ to $C_{100}$ hydrocarbons, $C_1$ to $C_{100}$ oxygenated hydrocarbons (e.g., alcohols), or a combination thereof, or any range including and in between any carbon number between $C_1$ and $C_{100}$; for example, the synthetic product may include $C_{10}$-$C_{14}$ hydrocarbons. In addition, reference to a "$C_2$+ hydrocarbon," a "$C_2$+ alcohol," or similar expressions refer to a $C_2$ to $C_{100}$ hydrocarbon or $C_2$ to $C_{100}$ alcohol, respectively, or any range including and in between any carbon number between $C_2$ and $C_{100}$. In any of the embodiments described herein, the synthetic product may predominantly include one or more compounds selected from $C_1$ to $C_{50}$ hydrocarbons, $C_1$ to $C_{50}$ oxygenated hydrocarbons, or combinations thereof. "Predominantly" as used herein means at least about 51 weight percent ("wt %") of the synthetic product. The synthetic product of the present technology may include one or more compounds selected from $C_1$ to $C_{50}$ hydrocarbons, $C_1$ to $C_{50}$ oxygenated hydrocarbons, or combinations thereof in an amount of about 51 wt % to about 100 wt %, or any range including and in between any integer between these two values. Thus, in some embodiments the synthetic product includes 40 wt % of $C_{14}$-$C_{18}$ hydrocarbons; in some embodiments the synthetic product includes 70 wt % of $C_1$-$C_4$ monohydroxyalkanes (i.e., monohydric alcohols).

The term "thermal communication" refers to at least two bodies, for example, two conduits or two microchannels, that may or may not be in physical contact with each other or adjacent to each other but still exchange heat with each other. One body in thermal communication with another body may heat or cool the other body.

The term "fluid" refers to a gas, a liquid, a mixture of a gas and a liquid, or a gas or a liquid, wherein the fluid may further contain dispersed solids, liquid droplets and/or gaseous bubbles. The droplets and/or bubbles may be irregularly or regularly shaped and may be of similar or different sizes.

"Controlled flow communication" as used herein will be understood to describe a flow from a first region to a second region of a fluid, where one or more aspects of the flow, such as the flow rate, pressure, and temperature, are set and controlled so that the flow is not necessarily dictated by equilibrium. The term also encompasses periods where the flow is temporarily discontinued, i.e., a flow rate of 0.

II. The Present Technology

Steam reforming, in general, is a method for producing CO and $H_2$ from hydrocarbon sources such as natural gas. In steam reforming, methane and steam are reacted in the presence of a catalyst to form a mixture of carbon monoxide and hydrogen according to the following chemical equation:

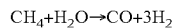

Steam reforming is an endothermic reaction that requires heating. The CO and $H_2$ may be used together as a syngas to produce a variety of synthetic products. However, the synthetic reactions employed to produce the synthetic products fail to utilize all the reactant CO. $CO_2$ may be produced in steam reforming as well as in the subsequent synthetic reaction. This remaining $CO_2$ downstream of the steam reforming and/or synthetic reaction must be taken into account, both in terms of process management as well as cost. In fact, $CO_2$ is often expelled as a waste product. In addition, $H_2O$ from the synthetic reactions and/or remaining in the steam reformed product must be managed, where management of such $H_2O$ typically includes costly and energy-intensive clean-up procedures, disposal, or both.

The present technology provides processes that not only manage CO and $CO_2$ downstream of reforming and/or synthetic processes, but also uses them as resources to advantageously produce useful products and/or facilitate other processes. Moreover, the carbon efficiency of the overall process may be further enhanced by addition of energy to this downstream $CO_2$, facilitating conversion of the $CO_2$ into CO that may be used in a synthetic process. The present technology optionally provides for use and generation of $H_2$ downstream of reforming and/or synthetic processes that further enhances the productivity and efficiency of the overall process. The present technology also optionally provides for the use of $H_2O$ downstream of the steam reforming process and/or $H_2O$ downstream of the synthetic reaction to facilitate production of useful products.

Thus, in an aspect, the present technology provides a steam reforming process that involves steam reforming a first reforming feed to produce a steam reformed product that includes $H_2$ and CO ("the steam reforming step"); optionally subjecting a second reforming feed that includes the steam reformed product to a second reforming step to provide a second reformed product that includes $H_2$ and CO; and contacting the $H_2$ and CO with a synthesis catalyst to produce a synthetic product and a tail gas ("the contacting step"). The initial mole ratio of $H_2$ to CO fed to the contacting step may be in the range from about 1.0:1 to about 2.1:1, or from about 1.5:1 to about 2.1:1, or from about 1.6:1 to about 2:1, or from about 1.6:1 to about 1.9:1. Heat for the steam reforming step is provided by combustion. Such combustion involves flowing a combustion gas (which includes $H_2$) over a permeate surface of an ion transport membrane and flowing an $O_2$-containing gas over a retentate surface of an ion transport membrane to react the combustion gas, produce heat, and produce an exhaust gas ("the combustion step"). The exhaust gas includes $H_2O$. The synthetic product includes one or more compounds selected from $C_1$ to $C_{100}$ hydrocarbons, $C_1$ to $C_{100}$ oxygenated hydrocarbons, or a combination thereof; the tail gas includes $CO_2$.

Notably, in the steam reforming process of the present technology, carbon downstream of the steam reforming step, second reforming step, and/or contacting step is reclaimed and reintroduced into the process to generate the synthetic product. This reclamation allows for otherwise waste carbon to be incorporated into the synthetic product. Such reclamation may involve reacting at least a portion of the tail gas in a water-gas shift ("WGS") reaction to produce more $CO_2$ and directing this to the steam reforming step. The WGS reaction converts CO and $H_2O$ into a WGS product that includes $CO_2$ and $H_2$. The WGS reaction may include a portion of $H_2O$ from the steam reformed product, a portion of $H_2O$ from the second reformed product, a portion of $H_2O$ produced in the contacting step, or a combination of any two or more thereof. WGS reactions, WGS catalysts, and WGS reactors are known to one skilled in the art and include high temperature WGS reactions and low temperature WGS reactions. WGS catalysts typically include, but are not limited to, metals and/or metal oxides of Cu, Zn, Fe, Cr, Mn, Mo, and combinations of any two or more thereof. The WGS catalysts may also include a support material, such as an aluminum oxide or a cerium oxide. For example, the WGS catalyst may include CuZn on an $Al_2O_3$ support, or the WGS catalyst may include FeCr on a $Ce_2O_3$ support. Incorporation of a WGS reaction further enhances the carbon recovery by providing a higher concentration of $CO_2$ than would otherwise be present in the tail gas. The $CO_2$ may be heated to further facilitate conversion of the $CO_2$ into CO in the steam reforming step and/or second reforming step, thereby increasing the carbon efficiency of the overall process.

More specifically, in the presently disclosed steam reforming process the first reforming feed includes $CH_4$ and the first and/or the second reforming feed (when the second reforming feed is present) includes one or more of (1) $CO_2$ separated from the steam reformed product and/or the second reformed product, (2) $CO_2$ separated from the tail gas, or (3) $CO_2$ formed from subjecting at least a portion of the tail gas to a WGS reaction which forms a WGS product that includes the $CO_2$.

Collectively, (1)-(3) above will be referred to as "downstream $CO_2$".

Furthermore, in the steam reforming process of the present technology, $H_2$ downstream of the steam reforming step, the second reforming step, or from the WGS reaction may be reclaimed. This reclaimed $H_2$ further enhances the efficiency and productivity of the presently disclosed technology. In particular, the combustion gas of the presently disclosed steam reforming process may include one or more of (i) $H_2$ separated from the steam reformed product and/or the second reformed product, (ii) $H_2$ separated from the tail gas, or (iii) $H_2$ formed from subjecting at least a portion of the tail gas to a WGS reaction (collectively, (i)-(iii) above will be referred to as "downstream $H_2$").

In such embodiments; the exhaust gas includes $H_2O$ produced from downstream $H_2$. In any of the above embodiments, it may be that the first reforming feed and/or the second reforming feed include the exhaust gas produced from this downstream $H_2$. By utilizing downstream $H_2$ in the combustion gas, the amount of $H_2O$ that may otherwise need to be added in the form of steam to the first reforming feed, the second reforming feed, or both, may be reduced or otherwise avoided completely by use of the exhaust gas.

Independently of whether downstream $H_2$ is included in the combustion gas, downstream $H_2$ (either (i), (ii), (iii), or any combination of any two or more thereof) may also be incorporated in the first reforming feed, the second reforming feed, or both. In any of the above embodiments, it may be that the first reforming feed and/or the second reforming feed include the exhaust gas. In such embodiments, the exhaust gas may further include $CO_2$ and the combustion gas further includes any one or more of $CO_2$ separated from the steam reformed product and/or the second reformed product, $CO_2$ separated from the WGS product, or $CO_2$ separated from the tail gas.

By way of example, the first reforming feed may include $CH_4$ and the second reforming feed include $H_2O$ and $CO_2$ where both the $H_2O$ and $CO_2$ are from the exhaust gas, where the combustion gas used to produce the exhaust gas included $CO_2$ separated from the WGS product. As another example, the first reforming feed may include $CH_4$ as well as $CO_2$ separated from the second reformed product. Another example includes where the first reforming feed includes $CH_4$ and the second reforming feed includes $CO_2$ separated from the second reformed product. As yet another example, the process may involve a first reforming feed that includes $CH_4$ and the second reforming feed includes $CO_2$ separated from the second reformed product as well as $CO_2$ separated from the WGS product.

The tail gas of the steam reforming process originates from an exit gas produced by the contacting step, where subsequent to the contacting step the exit gas is cooled and $H_2O$, light hydrocarbons (e.g., $C_2$-$C_4$ hydrocarbons), and any volatile oxygenated hydrocarbons (e.g., with a boiling point less than 100° C.) are removed from the exit gas to provide the tail gas. Such cooling may be accomplished by a variety of methods well known to one of skill in the art and/or by utilizing the exit gas as a heat exchange fluid, as described more fully herein.

Referring now to the figures, FIG. 1 illustrates the syngas generation portion of an integrated gas-to-products facility incorporating a process according to several embodiments of the steam reforming process, where the steam reforming feed includes an exhaust gas from a combustion chamber. As discussed more fully herein, FIG. 1 also illustrates how the present technology utilizes $CO_2$ and optionally $H_2$ provided by a WGS reaction of the tail gas to enhance the carbon efficiency of the process. FIG. 1 further illustrates an optional start-up procedure for the integrated facility that greatly reduces energy demands in comparison to a typical start-up.

In FIG. 1, natural gas feed 101, steam feed 102, and optionally tail gas recycle 103 are combined to make pre-reformer feed 105. Natural gas feed 101 predominantly includes methane ($CH_4$), and tail gas recycle 103 includes at least a portion of the tail gas. The mole ratio of steam to reformable carbon (such as $CH_4$ and not $CO_2$) in pre-reformer feed 105 may be about 3.0 or less, preferably about 0.6 to about 0.4. Pre-reformer feed 105 is directed to heat exchanger 240, where the temperature of pre-reformer feed 105 is raised. Heat exchangers of the present technology include, but are not limited to, heat exchange networks as well as heat exchange units. A heat exchange network may further include two or more heat exchange units. Heat exchangers may be 2-stream heat exchangers, 3-stream heat exchangers, or multi-stream heat exchangers.

Pre-reformer feed 105 may be raised to a temperature from about 350° C. to about 550° C. prior to introduction to pre-reformer 250; for the purposes of this illustration, the temperature of pre-reformer feed 105 is raised to about 420° C. Pre-reformer 250 converts $C_2$+ hydrocarbons present in pre-reformer feed 105 (originating from light hydrocarbons in natural gas feed 101) into $H_2$ and CO. Because the reactions in pre-reformer 250 are typically endothermic for the system, the temperature of pre-reformer product 108 is typically lower than that of pre-reformer feed 105. For the purposes of this illustration, pre-reformer product 108 exits pre-reformer 250 at a temperature of about 380° C. The temperature of the pre-reformer product 108 may be raised via heater 260 so that, when combined with exhaust gas 127 (including downstream $CO_2$ and $H_2O$ generated from downstream $H_2$) and optionally reclamation stream 160 (including downstream $CO_2$ and/or downstream $H_2$, as discussed more fully herein), reformer feed 110 is at a temperature sufficient for introduction into steam reformer 270. However, due to inclusion of downstream $H_2$, exhaust gas 127 may be at a temperature such that the heat provided by heater 260 is minimal or such that heater 260 may be off altogether. Thus, when downstream $H_2$ is utilized in the combustion gas, additional heat input may not be required for the subsequent reforming. Reformer feed 110 may be at a temperature of about 450° C. to about 750° C.; for the purposes of this illustration, reformer feed 110 is at a temperature of about 650° C. Heaters discussed herein may be any known to one of skill in the art, including but not limited to a natural gas fueled heater, a $C_2$+ hydrocarbon fueled heater, a methanol fueled heater, a hydrogen fueled heater, an electric heater, or a heater using a combination of fuels.

In the process of the present technology, a pre-reforming step is optional. As illustrated by FIG. 1, the first reforming feed includes methane ($CH_4$) and $H_2O$ as steam, where the steam may be provided by the exhaust gas (e.g., exhaust gas 127) and/or steam not produced in the combustion step. Where the first reforming feed includes the exhaust gas, the amount of additional steam (not from the combustion step) utilized may be reduced and, in some cases, not be included in the first reforming feed. The molar ratio of steam to reformable carbon (such as $CH_4$ and not $CO_2$) in the first reforming feed may be at least about 1.5, preferably at least about 3.0, and preferably no more than about 4.0. Any embodiment of the process may optionally involve recycling a portion of the tail gas to the pre-reforming and/or the steam reforming step, as illustrated by tail gas recycle 103. The recycled tail gas may include $H_2$ and CO with a molar ratio of $H_2$ to CO in a range from about 0.5:1 to about 0.7:1, or to about 0.8:1, or to about 0.9:1. The recycled tail gas is preferably pre-treated to recover $C_3$+ hydrocarbons and to minimize CO and ethylene components.

Exhaust gas 127 is provided by combustion chamber 280. Steam reformer 270 and combustion chamber 280 are contained in reforming enclosure 290. Combustion chamber 280 employs an ion transport membrane to supply oxygen from air stream 128 to combustion gas 126 in order to provide radiant heat (190) to steam reformer 270 and exhaust gas 127. Compositions of suitable ion transport membranes and methods of making such membranes are known to one of skill in the art. Ion transport membranes generally include, but are not limited to, a metal oxide such as a manganese oxide, a magnesium oxide, an aluminum oxide, a silicon oxide, a zinc oxide, a copper oxide, a nickel oxide, a cobalt oxide, an iron oxide, a titanium oxide, yttrium oxide, a zirconium oxide, a niobium oxide, a ruthenium oxide, a rhodium oxide, a palladium oxide, a silver oxide, an indium oxide, a tin oxide, a lanthanum oxide, an iridium oxide, a platinum oxide, a gold oxide, a cerium oxide, a neodymium oxide, a praseodymium oxide, an erbium oxide, a dysprosium oxide, a terbium oxide, a strontium oxide, a samarium oxide, a lutetium oxide, a gadolinium oxide, a ytterbium oxide, a europium oxide, a holmium oxide, a scandium oxide, or a combination of any two or more thereof. Ion transport membranes may be used in a variety of shapes, such as tubes or plates. For example, in the steam reforming process, the ion transport membrane may be a tube. In such embodiments, the permeate surface may be the interior of the tube and the retentate surface may be the exterior of the tube.

When using an ion transport membrane, flowing the $O_2$-containing gas (for FIG. 1, air stream 128) over the retentate surface of the ion transport membrane typically involves pressures from about 10 psig to about 150 psig, or any range including and in between any integer between these two values. As illustrated by air stream 128, it may be that the $O_2$-containing gas includes air, where the air may be $O_2$-enriched air. The $O_2$-containing gas may be about 0.1% to about 50% $O_2$ on a molar basis, or any range including and in between any two integers between these two values. The $O_2$-containing gas may be at a pressure from about 10 psig to about 150 psig, or any range including and in between any two integers between these two values. The combustion gas may be at a pressure from about 20 psig to about 500 psig, or any range including and in between any two integers between these two values.

In any embodiment described herein the combustion step may, if desired, be carried out in the presence of a combustion catalyst. Exemplary combustion catalysts may include one or more noble metals (e.g., Pt, Rh, Pd, Co, Cu, Mn, Fe, Ni), oxides of any such noble metal, perovskites, and/or aluminates. Such combustion catalysts may further include an activity-enhancing promoter such as Ce, Tb, Pr, oxides thereof, or a combination of any two or more thereof, and may include a suitable support. The suitable support may include $Al_2O_3$, MgO, $MgAl_2O_3$, $SiO_2$, $ZrO_2$, $TiO_2$, or a combination of any two or more thereof. The combustion catalyst may be disposed on the permeate surface of the ion transport membrane. For example, the combustion catalyst may reside on the permeate surface of the ion transport membrane or the combustion catalyst may be dispersed on the permeate surface of the ion transport membrane. That the combustion catalyst material may be "dispersed on" the permeate surface includes the conventional understanding that microscopic catalyst particles may be dispersed: on the permeate surface, in crevices of the permeate surface, and/or in open pores in the permeate surface. It may be that the combustion catalyst is chemically bonded to the permeate surface of the ion transport membrane.

Air steam 128 may be heated prior to supplying oxygen, such as by preheating in heat exchanger 240 via heat transfer with steam reformed product 115, and/or by heater 291. Heating air stream 128 is particularly advantageous because it minimizes the required membrane surface area since less oxygen is required to produce combustion heat. Such high temperatures may be accomplished, for example, by use of a heater with an electric heating element. Thus, heater 291 may preferably include an electric heating element. Combustion chamber 280 also provides an $O_2$-depleted air stream 129 that may be used for synthesis catalyst regeneration or to supply heat for other processes. This process is particularly suited to using $O_2$-depleted air stream for synthesis catalyst regeneration in the case where multiple parallel reformer and/or contacting trains are utilized (discussed in more detail herein). For example, the $O_2$-depleted air stream from one reformer train which is operating in normal production can directly supply flow to a separate contacting train which is undergoing regeneration. In regard to any embodiment of the process, the process involves net permeation of oxygen through the ion transport membrane from the retentate surface to the combustion gas. Thus, the net effect is the ionic transportation of oxygen from the retentate surface to the permeate surface, and therefore flowing the $O_2$-containing gas over the retentate surface in the combustion step produces an $O_2$-depleted gas. It should be noted in any embodiment the flow of the combustion gas may be co-current, counter-current, or cross-current to the flow of the $O_2$-containing gas. The temperature of the $O_2$-depleted gas, such as $O_2$-depleted air stream 129, may be from about 600° C. to about 1,200° C. The $O_2$-depleted gas may be at a temperature of about 600° C., about 650° C., about 700° C., about 750° C., about 800° C., about 850° C., about 900° C., about 950° C., about 1,000° C., about 1,050° C., about 1,100° C., about 1,150° C., about 1,200° C., or any range including or in between any two of these values. The $O_2$-depleted gas may be about 0% to about 20% $O_2$ on a molar basis, or any range including and in between any two integers between these two values; in some embodiments the $O_2$-depleted gas is substantially free of $O_2$.

Exhaust gas 127 exits combustion chamber 280, where exhaust gas 127 includes $H_2O$ and $CO_2$. As discussed above, pre-reformer product 108 is combined with exhaust gas 127 to produce reformer feed 110. Reformer feed 110 undergoes a steam reforming reaction in steam reformer 270 to produce steam reformed product 115. Steam reformer 270 includes a steam reforming catalyst. Such steam reforming catalysts are known to one of skill in the art. For example, the steam reforming catalyst may include Ni, Ru, Rh, Pd, Ir, Pt, or a combination of any two or more thereof, and may also include at least one of Au, Ag, Sn, Cu, Co, Mo, Fe, Gd, or B. The active catalyst material or metal may be supported. Such supports may include $Al_2O_3$, MgO, $MgAl_2O_4$, $CeO_2$, $SiO_2$, $ZrO_2$, $TiO_2$, or a combination of any two or more thereof. In any of the embodiments described herein, it may be that the heat for the steam reforming step includes radiant heat from the combustion step. In any of the embodiments of the process described herein, the heat for the steam reforming step may be at least partially provided by the $O_2$-depleted gas. Providing the heat via the $O_2$-depleted gas may involve a heat exchanger as described more fully herein. The heat exchanger may thus be used to cool the $O_2$-depleted gas prior to using the $O_2$-depleted gas in other applications.

Steam reformed product 115 includes syngas (i.e., $H_2$ and CO), $CO_2$, and $H_2O$. Steam reformed product 115 exits steam reformer 270 at a temperature in the range of about 850° C. to about 920° C. and a pressure in the range of about 10 bar to about 40 bar, more preferably about 15 bar to about 20 bar. For the purposes of this illustration, steam reformed product 115 exits steam reformer 270 at a temperature of about 920° C. and a pressure of about 15 bar. Steam reformed product 115 is then directed to heat exchanger 240 where reformed product 115 is cooled and water is removed via water separation unit 201 to provide raw syngas 117.

Thus, in any of the embodiments described herein and as illustrated in FIG. 1, it may be that the process involves flowing the steam reformed product through a heat exchanger to lower the temperature of the steam reformed product prior to the contacting step. Flowing the steam reformed product through a heat exchanger may involve flowing the steam reformed product through a first conduit and flowing a heat exchange fluid through a second conduit where the reformed product and heat exchange fluid are in thermal communication. In any of the above embodiments, it may be that flowing the steam reformed product through a heat exchanger involves flowing the steam reformed product through a first conduit; flowing a first heat exchange fluid through a second conduit; and flowing a second heat exchange fluid through a third conduit; where the steam reformed product and at least one of the first heat exchange fluid or the second heat exchange fluid are in thermal communication. In any of the above embodiments, it may be the heat exchanger involves flowing the steam reformed product through the first conduit and flowing a plurality of heat exchange fluids through a plurality of other conduits. Furthermore, in any of the embodiments described herein, any of the conduits, including the heat exchange conduits, may be microchannels. Processes for heat exchange in general and in particular relating to heat exchange processes involving microchannels are described in International Publication WO 2004/016347, incorporated herein by reference in its entirety for any and all purposes. The heat exchange fluid may include any one or more of air, steam, liquid water, gaseous nitrogen, other inert gases, syngas, molten salt, oils such as mineral oil, a gaseous hydrocarbon, a liquid hydrocarbon, a heat exchange fluids such as Dowtherm A and Therminol which are available from Dow-Union Carbide, or a mixture of two or more thereof. "Dowtherm" and "Therminol" are trademarks. In any of the embodiments described herein, it may be the heat exchange fluid includes any one or more of the $O_2$-containing gases, $O_2$-depleted gases, steam reformed product, second reformed product, WGS product, $CO_2$-containing streams, and tail gases described herein. Heat exchange network analysis methods are known to those skilled in the art to optimize the transfer of heat from process streams requiring cooling to those steams requiring heating.

Turning back to FIG. 1, upon exiting water separation unit 201, raw syngas 117 may then be pressurized via compressor 220 and subsequently sent to $CO_2$ absorption unit 202 to provide purified syngas stream 119. $CO_2$ separation according to the present technology may involve a $CO_2$ separation network and may occur by $CO_2$ sorption and subsequent stripping, $CO_2$ adsorption and desorption, and/or $CO_2$ removal membranes, where FIG. 1 illustrates an embodiment utilizing $CO_2$ absorption ($CO_2$ sorption unit 202) and $CO_2$ stripping ($CO_2$ stripping unit 203). Purified syngas stream 119 may then be combined with adjusted syngas stream 131 (enriched in CO) to optimize the molar ratio of $H_2$ to CO, which for purposes of this illustration is 1.95:1 on a molar basis, to produce syngas stream 120. Syngas stream 120 is then directed to a contacting step (not shown). The amount of adjusted syngas stream 131 provided is controlled to provide the desired target ratio of $H_2$ to CO, and may be discontinued if needed. In any of the above embodiments of the process described herein, the initial mole ratio of $H_2$ to CO fed to the contacting step may be in the range of about 0.5:1 to about 4:1. The initial mole ratio of $H_2$ to CO fed to the contacting step may be about 1.4:1 to about 2.1:1, or from about 1.5:1 to about 2.1:1, or from about 1.6:1 to about 2:1, or from about 1.6:1 to about 1.9:1. Where the adjusted syngas stream 131 is not combined with the purified syngas stream 119, then the purified syngas stream 119 is syngas stream 120.

Although not shown, the process may involve including a portion of the tail gas in the contacting step. The volumetric ratio of the syngas including $H_2$ and CO from other sources (e.g., the steam reformed product or the second reformer product) to the portion of the tail gas in the contacting step may be in the range of about 0.5:1 to about 10:1, or from about 1:1 to about 8:1, or from about 1:1 to about 6:1, or from about 1:1 to about 4:1, or from about 3:2 to about 7:3, or about 2:1.

In any of the above embodiments, the process may involve flowing the portion of the tail gas through a heat exchanger to raise the temperature of the tail gas prior to recycling it to the steam reforming step, to the second reforming step, to the contacting step, including it in the combustion step and/or subjecting it to a WGS reaction. In any of the above embodiments, flowing the tail gas through a heat exchanger may involve flowing the tail gas through a first conduit and flowing a heat exchange fluid through a second conduit where the tail gas and heat exchange fluid are in thermal communication. While heat exchange fluids are described more fully below, the heat exchange fluid may include any one or more of air, the steam reformed product, the second reformed product, $H_2O$, the $O_2$-containing gas, or the $O_2$-depleted gas provided by any one of the embodiments described herein. Flowing the tail gas through a heat exchanger may involve flowing the tail gas through a first conduit, flowing a first heat exchange fluid through a second conduit, and flowing a second heat exchange fluid through a third conduit, where the tail gas and at least one of the first heat exchange fluid or the second heat exchange fluid are in thermal communication. The first heat exchange fluid and the second heat exchange fluid may be different fluids or may be the same fluid. In any of the above embodiments, it may be flowing the tail gas through a heat exchanger involves flowing the tail gas through the first conduit and flowing a plurality of heat exchange fluids through a plurality of other conduits.

Hydrogen-containing stream 134 arises in part from $H_2$-rich stream 140. $H_2$-rich stream 140 is provided by hydrogen separation network 200. The $H_2$ of $H_2$-rich stream 140 is separated from a WGS product produced from tail gas (130) and/or slipstream 121 by hydrogen separation network 200. The hydrogen separation network of the present technology may involve hydrogen removal membranes, rely on pressure swing adsorption, and/or rely on temperature swing adsorption. Hydrogen separation network 200 may also be a single unit or multiple hydrogen separation units. In any of the embodiments described herein it may be that the combustion gas includes $H_2$ provided by the WGS product. Thus, the combustion gas may include the WGS product, or (as illustrated by FIG. 1) prior to use in the combustion gas, the $H_2$ may be separated from the WGS product by a hydrogen separation network. In the illustration provided in FIG. 1, hydrogen removal membranes in hydrogen separation network 200 initially provide a $H_2$-rich stream at a purity less than about 95% (on a molar basis) and provide adjusted syngas stream 131 (enriched in CO). A portion of the $H_2$-rich stream with the purity less than about 95% may be used as $H_2$-rich stream 140. $H_2$-rich streams, separated from the steam reformed product, the second reformed product, and/or the WGS product from the tail gas, or portions thereof may be utilized in the steam reforming step, the second reforming step, the combustion step, and/or the contacting step. The $H_2$-rich stream or portion thereof may then be directed to pressure swing adsorption or temperature swing adsorption to provide high purity $H_2$ stream 141. High purity $H_2$ stream 141 may be at a purity of greater than about 95% (on a molar basis), preferably greater than about 98%, and may have less than about 0.5% $N_2$. High purity $H_2$ stream 141 may be used in processes where such high purity $H_2$ is desirable, including but not limited to synthesis catalyst regeneration, synthesis catalyst rejuvenation, or hydroprocessing reactions known in the art and as discussed herein. Hydrogen separation network 200 may also provide fuel gas stream 132 for use in other applications and to purge inert components such as nitrogen.

Notably, hydrogen-containing stream 134 also includes $CO_2$ provided by $CO_2$ stream 138 from $CO_2$ stripping unit 203. Such a process allows for recycling of valuable carbon back to steam reformer 270 via combustion gas 126, where the recycled $CO_2$ may be reacted in steam reformer 270 to yield CO and the CO incorporated in syngas stream 120 for producing hydrocarbons. $CO_2$ stream 138 may be pressurized by compressor 222. A portion of the product of the WGS reaction (150) may also be utilized: portion 150 may be pressurized by compressor 223 and combined with $CO_2$ stream 138 and $H_2$-rich stream 140 to produce hydrogen-containing stream 134. The amount of portion 150, $CO_2$ stream 138, and $H_2$-rich stream 140 used to produce hydrogen-containing stream 134 is controlled to provide the desired concentrations of $H_2$ and $CO_2$ in hydrogen-containing stream 134. In fact, either portion 150 or $CO_2$ stream 138 may be discontinued, but both are not discontinued, unless optional reclamation stream 160 is utilized as discussed herein. Although not shown, hydrogen-containing stream 134 may be directed to heat exchanger 240 to raise the temperature prior to combination with syngas slipstream 125 or use as combustion gas 126. Similarly, combustion gas 126 may be directed to heat exchanger 240 to raise the temperature prior to introduction to combustion chamber 280. An advantage from shifting the tail gas is that this shifted gas may then be heated to a higher temperature without using exotic metallurgy (e.g., alloy compositions with relatively high Ni and Cr content, such as Inconel)—that is, the shifted gas is of such a composition that less expensive materials may be used in construction of conduits and apparatuses that contain the shifted gas when heating to higher temperatures. It is also possible to direct some of the tail gas to the combustion chamber at a lower temperature (below about 300° C.). The shifted tail gas may also be subjected to a hydrogenolysis or a hydrogenation reaction to facilitate heating without coke formation.

It is to be noted that high concentrations of $CO_2$ in combustion gas 126 may cause the composition or stoichiometry of the ion transport membrane of combustion chamber 280 to change, for example, by reaction with the $CO_2$. Exemplary membranes involved in such a reaction with $CO_2$ are those including, for example, alkaline earth metals (e.g., Ca). The decomposition of the ion transport membrane in the presence of $CO_2$ can be expressed in terms of the $CO_2$ partial pressure at equilibrium conditions, which may be defined as the critical threshold. While at $CO_2$ partial pressures less than the critical threshold, decomposition via $CO_2$ reactions may be acceptably low or negligible. However, at $CO_2$ partial pressures greater than the critical threshold for the ion transport membrane, the ion transport membrane will change through reaction with $CO_2$. The value of the critical threshold is a function of temperature, oxygen partial pressure, and the composition of the ion transport membrane. Thus, in any of the above embodiments involving a combustion gas that includes $CO_2$, it may be the process further involves maintaining a partial pressure of $CO_2$ in the combustion gas that is below the critical threshold for the ion transport membrane used in the combustion step.

Optional reclamation stream 160 includes at least one portion of stream 150, $CO_2$ stream 138, or $H_2$-rich stream 140, where the amount of each is controlled to provide the desired concentrations of $H_2$ and $CO_2$ in optional stream 160. When employed, optional stream 160 may be (1) combined with pre-reformer feed 105 and both introduced to pre-reformer 250 to produce pre-reformer product 108, or (2) combined with pre-reformer product 108 and exhaust gas 127 to form reformer feed 110, or (3) both (1) and (2). For example, reformer feed 110 may include reclamation stream 160, where reclamation stream 160 includes $CO_2$ stream 138 such that downstream $CO_2$ is provided to steam reformer 270 to produce steam reformed product 115. Not only does combination with exhaust gas 127 raise the temperature of $CO_2$ stream 138 to further enhance the production of CO from the downstream $CO_2$, but this incorporation of downstream $CO_2$ after the combustion step allows for greater inclusion of downstream $CO_2$ should the ion transport membrane exhibit a critical threshold with respect to $CO_2$.

Notably, FIG. 1 illustrates three optional start-up procedures that each greatly reduce energy demands in comparison to a typical start-up.

In the first option, the reactor including the contacting step is not running, compressor 220 is off, and steam reformer 270 is not yet producing steam reformed product 115. In this first option, the reaction in combustion chamber 280 may be initiated with natural gas and/or a start-up fuel (such as $H_2$, a $C_{2+}$ hydrocarbon, or an oxygenated hydrocarbon) as the combustion gas (not shown). Gases are circulated using start-up compressor 221 to gradually increase temperature and begin production of steam reformed product 115 from steam reformer 270. Upon production of steam reformed product 115 and subsequent generation of raw syngas 117, low pressure syngas slipstream 125 would be substituted as combustion gas 126. In such a startup, syngas slipstream 125 may be pressurized in start-up compressor 221 prior to being introduced as combustion gas 126 in combustion chamber 280. When steam reformed product 115 is produced with a desired syngas flowrate and/or desired molar ratio of $H_2$ to CO, compressor 220 would be started to provide the pressure necessary for the contacting step. Either prior to start of compressor 220 (i.e., utilizing compressor 221) or alternatively after start of compressor 220, production of $CO_2$ stream 138 and $H_2$-rich stream 140 allow for hydrogen-containing stream 134 to be incorporated in combustion gas 126. Such incorporation allows for the amount of syngas slipstream 125 incorporated in combustion gas 126 to be reduced and eventually syngas slipstream 125 may be minimized or discontinued altogether. Syngas slipstream 125 may be reduced or discontinued in favor of hydrogen-containing stream 134 after startup of compressor 220.

In the second option, the reaction in combustion chamber 280 may be initiated with natural gas and/or the start-up fuel as the combustion gas (not shown) and the entire process, including the contacting step, performed with compressor 220 off. Similar to the first option, upon initial generation of raw syngas 117 (a portion of which is concurrently sent to the contacting step) low pressure syngas slipstream 125 would be substituted as combustion gas 126 where syngas slipstream 125 may be pressurized in start-up compressor 221. When steam reformed product 115 is produced with a desired syngas flowrate and/or desired molar ratio of $H_2$ to CO, compressor 220 would be started to provide a higher pressure for the contacting step and thus increase the efficiency of the contacting step. Subsequent production of hydrogen-containing stream 134 (either prior to or after start of compressor 220) allows for the amount of syngas slipstream 125 incorporated in combustion gas 126 to be reduced and eventually minimized or discontinued altogether. Much like the first option, syngas slipstream 125 may be reduced or discontinued in favor of hydrogen-containing stream 134 after startup of compressor 220.

Although not shown in FIG. 1, where multiple reforming enclosures are involved in supplying syngas stream 120, several reforming enclosures may contribute reformed products that are included with steam reformed product 115 in order to reach the desired syngas flowrate, pressure and/or desired molar ratio of $H_2$ to CO for the startup of compressor 220. Thus, with either a singular steam reformer 270 or by use of reforming enclosures/trains including a steam reformer and/or other reforming reactions, such a startup procedure (according to option 1 or option 2) allows for the use of a relatively small start-up compressor 221 in order to provide enough syngas at a sufficient pressure such that the energy demands of starting compressor 220 are greatly reduced.

The third option relies on multiple reforming enclosures, where either the first option or second option may or may not be employed, involving a first reforming enclosure and a first contacting step (a "first train"). Upon startup of this first train, downstream $H_2$ (from the first reforming enclosure and/or first train) would then be utilized to produce a hydrogen-containing stream (similar to 134) in a second reforming enclosure. Downstream $CO_2$ may also be incorporated into this hydrogen-containing stream. This second reforming enclosure may utilize the hydrogen-containing stream to provide the reaction in the combustion chamber of the second reforming enclosure and allow for steam reforming in the second reforming enclosure. The main compressor may be started once there is adequate flow from the raw syngas from one, two, or more reforming enclosures. This third option may also involve a second contacting step, where the second reforming enclosure utilizes the first or second option for starting up a main compressor for the second contacting step. The third option may likewise be employed with a plurality of reformer trains and contacting steps.

Other Reforming Processes According to the Present Technology

FIG. 1 provides an illustration involving steam reforming. However, further reforming processes may be employed to produce products that may be combined with the steam reformed product in order to provide the $H_2$ and CO to the contacting step, as well as to adjust the molar ratio of $H_2$ to CO.

For example, the process may involve two parallel steam reforming steps to produce two reformed products that are ultimately combined to provide the $H_2$ and CO to the contacting step. Further, it may be three or more reforming steps are utilized in parallel and/or in series to produce three or more syngas products that are ultimately combined to provide the $H_2$ and CO to the contacting step. In any of the above embodiments, it may be that the $H_2$ and CO to the contacting step include $H_2$ and CO derived from a partial oxidation reforming step, an autothermal reforming step, a $CO_2$ reforming (also known as "dry reforming") step, a coal gasification process, or combinations of any two or more thereof. With each of these, a product that includes $H_2$ and CO is produced, where the levels of $H_2$ and CO may be adjusted by separating $H_2$ from CO and/or other components using membranes or pressure swing adsorption.

Furthermore, in any of the above embodiments, the combustion step may be part of a partial oxidation reforming, an autothermal reforming, a dry reforming, or combinations of any two or more thereof and produce a syngas product that may be combined with a steam reformed product to provide the $H_2$ and CO to the contacting step. As noted previously, the exhaust gas of the combustion step may also be included as a steam reforming feed, and thus the exhaust gas would include a partial oxidation reformed product, autothermal reformed product, a dry reformed product, or combinations of any two or more thereof. For partial oxidation reforming, autothermal reforming, and/or dry reforming that includes the combustion step, it may be that the combustion step occurs first in a "combustion zone" followed by the reforming reaction in a "reforming zone."

However, the second reforming step may include the combustion step as part of the second reforming step. Thus, a partial oxidation reforming, an autothermal reforming, or a combination thereof may include the combustion step of the present technology, where the combustion gas of the combustion step would include a portion of the steam reformed product and the exhaust gas would be a second reformed product syngas. In such embodiments, the second reformed product would not be included in the steam reforming feed. This second reforming step may include the combustion step in a combustion zone followed by the second reforming reaction.

While the combustion zone as described herein would include the ion transport membrane, the reforming zone may or may not include an ion transport membrane. In some embodiments, the reforming zone includes the ion transport membrane of the combustion step. The combustion zone may further include a combustion catalyst as described herein. The combustion catalyst may be disposed on the permeate surface of the ion transport membrane in the combustion zone. For example, the combustion catalyst may reside on the permeate surface of the ion transport membrane or the combustion catalyst may be dispersed on the permeate surface of the ion transport membrane. That the combustion catalyst material may be "dispersed on" the permeate surface includes the conventional understanding that microscopic catalyst particles may be dispersed: on the permeate surface, in crevices of the permeate surface, and/or in open pores in the permeate surface. It may further be that a portion of the combustion catalyst is chemically bonded to the permeate surface of the ion transport membrane.

In any of the above embodiments, it may be that the $H_2$ and CO of the contacting step include $H_2$ and CO from an autothermal reformed product (ATR product) produced by autothermal reforming (ATR), referred to as an "autothermal reforming step" hereafter. In any of the above embodiments, it may be the second reforming step includes an autothermal reforming step. In any of the above embodiments, it may be the ATR step includes the combustion step of the process, and thus the second reforming feed includes the combustion gas and the second reformed product includes the exhaust gas. In such embodiments, the ATR step provides heat to the steam reforming step.

In any of the embodiments involving autothermal reforming, it may be the ATR step occurs in the presence of an ion transport membrane. This ion transport membrane is termed an autothermal reforming ion transport membrane (ATR-ITM). In such embodiments, the ATR may involve flowing an ATR feed over a permeate surface of the ATR-ITM and flowing an $O_2$-containing gas over a retentate surface of the ATR-ITM to produce the ATR product. At least one component of the ATR feed is $CH_4$. For example, where the ATR feed includes the steam reformed product, the steam reformed product may include $CH_4$ not consumed in the steam reforming reaction. An autothermal reforming catalyst may be disposed on the reformer surface of the ATR-ITM. The $O_2$-containing gas may be at a pressure from about 10 psig to about 150 psig, or any range including and in between any two integers between these two values. The ATR feed in contact with the permeate surface may be at a pressure from about 20 psig to about 500 psig, or any range including and in between any two integers between these two values. Flowing the $O_2$-containing gas over the retentate surface produces an ATR-ITM $O_2$-depleted gas. The temperature of the ATR-ITM $O_2$-depleted gas may be from about 600° C. to about 1,200° C., or any range including and in between any integer between these two values. The ATR-ITM $O_2$-depleted gas may be about 0% to about 20%

$O_2$ on a molar basis, or any range including and in between any two integers between these two values.

The ATR-ITM may be a separate structure from the ion transport membrane used in the process to react the combustion gas. However, in embodiments where the ATR step includes the combustion step of the process, the ATR-ITM is the ion transport membrane of the combustion step.

Figure 2:
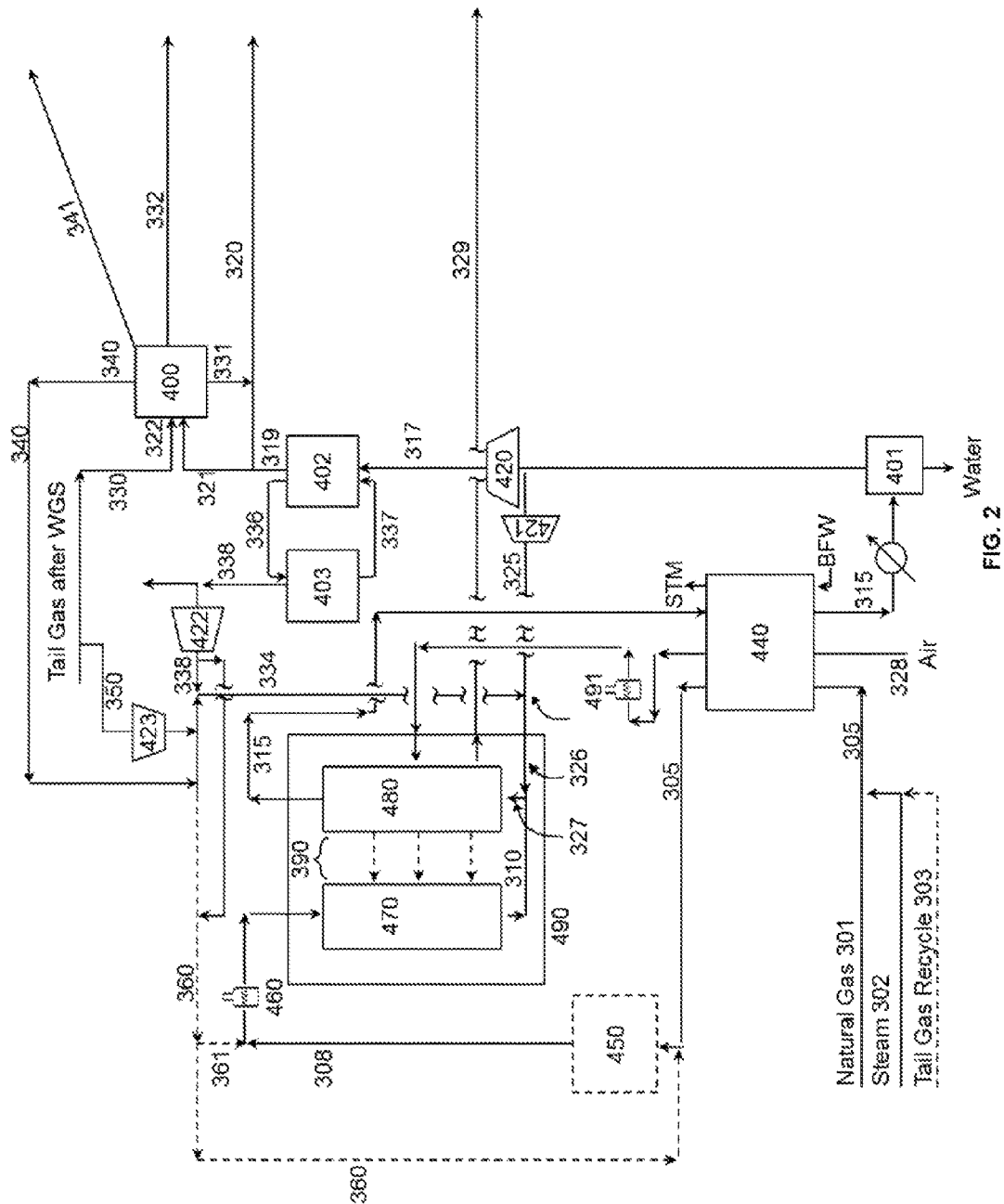
FIG. 2 illustrates a process involving steam reforming, where in the illustration the steam reformed product is combined with $CO_2$ downstream of the steam reforming step and fed to an autothermal reformer, according to several embodiments.

FIG. 2 provides an illustrative embodiment of the process involving ATR-ITM where the ATR step includes the combustion step. By utilizing autothermal reforming on the steam reformed product in combination with $CO_2$ containing feeds, the molar ratio of $H_2$ to CO may further be varied. FIG. 2 also illustrates how the present technology utilizes $CO_2$ and $H_2$ provided by a WGS reaction of the tail gas to enhance the carbon efficiency of the process. As discussed above, the present technology is not to be limited in terms of the particular figures described herein, which are intended as single illustrations of the present technology. Moreover, any element described in the embodiment of FIG. 1 may be utilized in a similar fashion in the embodiment of FIG. 2, and vice versa.

In FIG. 2, natural gas feed 301, steam feed 302, and an optional tail gas recycle 303 are combined to make pre-reformer feed 305. The mole ratio of steam to reformable carbon (such as $CH_4$ and not $CO_2$) in pre-reformer feed 305 may be about 3.0 or less, preferably about 0.6 to about 0.4. Natural gas feed 301 predominantly includes methane and the optional tail gas recycle 303, when employed, includes at least a portion of the tail gas. Pre-reformer feed 305 is directed to heat exchanger 440 to raise the temperature of the pre-reformer feed 305 about 420° C. prior to introduction to pre-reformer 450. Prior to the pre-reformer 450, pre-reformer feed 305 may be combined with reclamation stream 360 (which includes $CO_2$ and/or $H_2$ from downstream of the process, as discussed more fully below). Pre-reformer 450 produces pre-reformer product 308, which may optionally be combined with reclamation stream 361 (which includes $CO_2$ and/or $H_2$ from downstream of the process) and then directed to heater 460 to raise the temperature of pre-reformer product 308, e.g., to about 650° C., prior to introduction to steam reformer 470. Although not shown, it is also known in the art to recycle some tail gas 303 directly to the ATR feed. Recycled tail gas may be pre-treated to remove ethylene and $C_3+$ hydrocarbons. Notably, while FIG. 2 illustrates a pre-reforming step, such a pre-reforming step is optional.

Steam reformer feed 308 undergoes a steam reforming reaction in steam reformer 470 to produce steam reformed product 310. Although not shown, in any embodiment of the process a portion of the $H_2$ in the steam reformed product may be separated from the steam reformed product by a hydrogen separation network prior to further use of the steam reformed product. Steam reformed product 310 is combined with feed 326 to provide ATR feed 327, where ATR feed 327 is subjected to autothermal reforming in autothermal reformer 480 ("ATR 480"). In any embodiment described herein, it may be that the molar ratio of steam to reformable carbon (such as $CH_4$ and not $CO_2$) in the second reforming feed (such as ATR feed 327) may be about 0.6 or less, preferably about 0.6 to about 0.4. Although not shown in FIG. 2, any embodiment of the process may optionally involve recycling a portion of the tail gas to the second reforming step. The recycled tail gas may include $H_2$ and CO with a molar ratio of $H_2$ to CO in a range from about 0.5:1 to about 2:1, or from about 0.6:1 to about 1.8:1, or from about 0.7:1 to about 1.2:1. The volumetric ratio of stream 310 to the portion of the tail gas in the second reforming step may be in the range of about 0.5:1 to about 10:1, or from about 1:1 to about 8:1, or from about 1:1 to about 6:1, or from about 1:1 to about 4:1, or from about 3:2 to about 7:3, or about 2:1.

ATR 480 employs an ion transport membrane (an ATR-ITM) to supply oxygen from air stream 328 to ATR feed 327 in order provide ATR product 315. As part of the autothermal reforming reaction, ATR 480 also provides heat. Thus, the heat for the steam reforming reaction performed in steam reformer 470 includes heat provided by ATR 480. While not shown, ATR 480 may include a first combustion zone followed by an autothermal reforming zone. In such embodiments, the combustion zone may or may not include any one or more of the previously described combustion catalysts, where such combustion catalyst may be disposed on the ATR-ITM in addition to the autothermal reforming catalyst (described below) in the autothermal reforming zone. Steam reformer 470 and ATR 480 are contained in reforming enclosure 490. Air steam 328 may be heated prior to supplying oxygen, such as by preheating in heat exchanger 440 via heat transfer with ATR product 415 and/or by heater 491. Heating of air stream 328 by heater 491 more heat so that more methane and the $CO_2$ in ATR feed 327 may be converted to CO and the required membrane area is decreased since less heat is derived from combustion with transferred oxygen. ATR 480 also provides an $O_2$-depleted air stream 329 that may be used for catalyst regeneration or to supply heat for other processes. In any of the embodiments described herein, it may be that the heat for the steam reforming step (e.g., heat for steam reformer 470) includes heat supplied by the $O_2$-depleted gas, e.g., $O_2$-depleted air stream 329.

Autothermal reforming of the present technology involves an autothermal reforming catalyst. Autothermal reforming catalysts may include platinum, rhodium, ruthenium, or nickel, and may include an oxide support material. In any of the embodiments of the process described herein, the oxide support material of the autothermal reforming catalyst may include gadolinium-doped ceria (CGO). In any of the embodiments described herein, the autothermal reforming catalyst may include Rh—CGO, Rh—Pt—CGO, and/or $La_{0.8}Sr_{0.2}Cr_{0.9}Ni_{0.1}O_3$. As illustrated by FIG. 2, the second reforming feed (in this case, the ATR feed) may include one or more feed components, such as the steam reformed product, methane ($CH_4$), steam, a recycled tail gas component, etc. Any embodiment of the process may optionally involve recycling a portion of the tail gas to the second reforming step.

Although not shown in FIG. 2, in any of the embodiments of the present technology involving autothermal reforming, it may be that the ATR step includes (1) a first stage involving flowing the ATR feed over a permeate surface of the ATR-ITM and flowing the $O_2$-containing gas over a retentate surface of the ATR-ITM to produce an interstage product; and (2) a second stage involving flowing the interstage product over an interstage surface of a second ATR-ITM and flowing the $O_2$-containing gas over a retentate surface of the second ATR-ITM to produce the ATR product.

In any of the above embodiments involving autothermal reforming, the autothermal reforming step may include a plurality of stages to produce the ATR product. As illustrated in FIG. 2, one or more of these ATR stages may provide heat to the prior steam reforming step.

ATR product 315 includes syngas (i.e., $H_2$ and CO), $CO_2$, and $H_2O$. For the purposes of this illustration, the ATR product 315 exits ATR 270 at a temperature from about 940° C. to about 1,100° C. and is directed to heat exchanger 440. ATR product 315 is cooled in heat exchanger 440 such that water may be removed via water separation unit 401 to yield raw syngas 317. Raw syngas 317 may then be pressurized via compressor 420 and subsequently sent to $CO_2$ sorption unit 402 to generate purified syngas stream 319. Purified syngas stream 319 may then be combined with adjusted syngas stream 331 (enriched in CO) to optimize the molar ratio of $H_2$ to CO, which for purposes of this illustration is 1.95:1 on a molar basis, to produce the syngas stream 320. Syngas stream 320 is then directed to a contacting step (not shown). The amount of adjusted syngas stream 331 provided is controlled to provide the desired target ratio of $H_2$ to CO, and may be discontinued if needed.

Hydrogen separation network 400 provides adjusted syngas stream 331, where hydrogen separation network 400 is supplied by a slipstream from the purified syngas (321) and/or includes WGS product 330. WGS product 330 is yielded by performing a WGS reaction on a portion of the tail gas. In the illustration provided in FIG. 2, hydrogen removal membranes in hydrogen separation network 400 initially provide a $H_2$-rich stream at a purity less than about 95% (on a molar basis) and adjusted syngas stream 331 (enriched in CO). A portion of the $H_2$-rich stream with the purity less than about 95% may be used as $H_2$-rich stream 340. The $H_2$-rich stream or portion thereof may then be directed to pressure swing adsorption or temperature swing adsorption to provide high purity $H_2$ stream 341. High purity $H_2$ stream 341 may be at a purity of greater than about 95% (on a molar basis), preferably greater than about 98%, and may have less than about 0.5% $N_2$. High purity $H_2$ stream 341 may be used in processes where such high purity $H_2$ is desirable, including but not limited to synthesis catalyst regeneration, synthesis catalyst rejuvenation, or hydroprocessing reactions known in the art and as discussed herein. Hydrogen separation network 400 may also provide fuel gas stream 332 for use in other applications.

A portion of the product of the WGS reaction (350) may also be utilized directly. Portion 350 may pressurized by compressor 423 and combined with $CO_2$ stream 338 and $H_2$-rich stream 340 to produce hydrogen-containing stream 334. The amount of portion 350, $CO_2$ stream 338, and $H_2$-rich stream 340 used to produce hydrogen-containing stream 334 is controlled to provide the desired concentrations of $H_2$ and $CO_2$ in hydrogen-containing stream 334. In fact, either portion 350 or $CO_2$ stream 338 may be discontinued, but both are not discontinued unless optional reclamation stream 360 is utilized as discussed herein. Hydrogen-containing stream 334 may optionally be combined with syngas slipstream 325 (which is a portion of raw syngas stream 317) to provide feed 326; when syngas slipstream 325 is not used the composition of hydrogen-containing stream 334 is the composition of feed 326. As discussed above, feed 326 is combined with steam reformed product 310 to provide ATR feed 327. Although not shown, hydrogen-containing stream 334 may be directed to heat exchanger 440 to raise the temperature prior to combination with steam syngas slipstream 325 or use as feed 326. Similarly, feed 326 may be directed to heat exchanger 440 to raise the temperature prior to combination with steam reformed product 310 (not shown).

Optional reclamation stream 360 includes at least one of portion 350 or $CO_2$ stream 338, and may optionally include $H_2$-rich stream 340, where the amount of each is controlled to provide the desired concentrations of $H_2$ and $CO_2$ in optional reclamation stream 360. When employed, optional reclamation stream 360 may be (1) combined with pre-reformer feed 305 and both introduced to pre-reformer 450 to produce pre-reformer product 308, or (2) combined with pre-reformer product 308 and both introduced to steam reformer 470 to yield steam reformed product 310, or (3) both (1) and (2).

Similar to FIG. 1, FIG. 2 illustrates three optional start-up procedures that each greatly reduce energy demands in comparison to a typical start-up.

In the first option, the reactor including the contacting step is not running, compressor 420 is off, and steam reformer 470 is not yet producing steam reformed product 310, the autothermal reforming in ATR 480 may be initiated with natural gas and/or a start-up fuel (such as $H_2$, a $C_{2+}$ hydrocarbon, or an oxygenated hydrocarbon) as ATR feed 327 (not shown). Gases are circulated using start-up compressor 421 to gradually increase temperature and begin production of ATR reformed product 315 from steam reformer 470. Upon production of ATR product 315 and subsequent generation of raw syngas 317, low pressure syngas slipstream 325 would be incorporated as part of ATR feed 327. In such a startup, syngas slipstream 325 may be pressurized in start-up compressor 421 prior to being introduced in ATR 480. Upon sufficient heat generation by ATR 480, steam reforming via steam reformer 470 would be initiated. When ATR product 315 is produced with a desired syngas flowrate and/or desired molar ratio of $H_2$ to CO, compressor 420 would be started to provide the pressure necessary for the contacting step. Either prior to start of compressor 420 (i.e., utilizing compressor 421) or alternatively after start of compressor 420, subsequent production of $CO_2$ stream 338 and $H_2$-rich stream 340 allow for hydrogen-containing stream 334 to be incorporated in feed 326. Such incorporation allows for the amount of syngas slipstream 325 incorporated in ATR feed 327 to be reduced, and eventually syngas slipstream 325 may be minimized or discontinued altogether.

In the second option, the reaction in ATR 480 may be initiated with natural gas and/or the start-up fuel as ATR feed 327 (not shown) and the entire process, including the contacting step, performed with compressor 420 off. Similar to the first option, upon initial generation of raw syngas 317 (a portion of which is concurrently sent to the contacting step) low pressure syngas slipstream 325 would be incorporated as part of ATR feed 327. Subsequent production of hydrogen-containing stream 334 (either prior to or after starting compressor 420) allows for the amount of syngas slipstream 325 incorporated in ATR feed 327 to be reduced and eventually minimized or discontinued altogether. When ATR product 315 is produced with a desired syngas flowrate and/or desired molar ratio of $H_2$ to CO, compressor 420 would be started to provide a higher pressure for the contacting step and thus increase the efficiency of the contacting step.

Although not shown in FIG. 2, where multiple reforming enclosures are involved in supplying syngas stream 120, a portion of the reforming enclosures may contribute reformed products that are included with ATR product 315 in order to reach the minimum flow rate of $H_2$ to CO required for the startup of compressor 420. Thus, with either a singular steam reformer 470 and a singular ATR 480, or by use of reforming enclosures/trains including additional steam reformers and/or other reforming reactions, such a startup procedure allows for the use of a relatively small start-up compressor 421 in order to provide enough syngas at a sufficient pressure such that the energy demands of starting main compressor 420 are greatly reduced.

Similar to the discussion regarding FIG. 1, the third option relies on multiple reforming enclosures, where either the first option or second option may or may not be employed, involving a first reforming enclosure and a first contacting step (a "first train"). Note that there may or may not be multiple contacting steps. Upon startup of this first train, a portion of the tail gas from the first contacting step would be subjected to the WGS reaction. A portion of downstream $H_2$ (from the first reforming enclosure and/or first train) may then be utilized to produce hydrogen-containing stream (similar to 334) in a second reforming enclosure. Downstream $CO_2$ may also be incorporated into this hydrogen-containing stream. This second reforming enclosure would utilize the hydrogen-containing stream to initiate an autothermal reforming reaction in the second reforming enclosure and subsequently allow for steam reforming in the second reforming enclosure. The main compressor may be started once there is adequate flow from the raw syngas from one, two, or more reforming enclosures. This third option may also involve a second contacting step, where the second reforming enclosure utilizes the first or second option for starting up a main compressor for the second contacting step. The third option may likewise be employed with a plurality of reformer trains and contacting steps.

Catalyst Regeneration

As noted in FIGS. 1 and 2, high purity $H_2$ separated from the steam reformed product, the second reformed product, and/or the WGS product from the tail gas (e.g., hydrogen stream 141/341) may be used to supply hydrogen to a periodic synthesis catalyst rejuvenation step (when the synthesis catalyst includes a Fischer-Tropsch catalyst), a periodic synthesis catalyst regeneration step (when the synthesis catalyst includes a Fischer-Tropsch catalyst), or a hydroprocessing step.

Thus, the process may include a periodic synthesis catalyst rejuvenation step when the synthesis catalyst includes a Fischer-Tropsch catalyst (described in more detail herein). In the periodic synthesis catalyst regeneration step, the contacting step employing the synthesis catalyst to be rejuvenated is discontinued for the duration of the synthesis catalyst rejuvenation step. "Periodic" as used herein will be understood to mean occurring after a particular increase in temperature of the contacting step to maintain a constant percent conversion of CO by the synthesis catalyst. The particular increase in temperature may be at least about 5° C. as compared to a temperature previously employed for the same percent conversion of CO. The particular increase in temperature may be at least about 5° C., or at least about 10° C., or at least about 15° C., or at least about 20° C., or about 30° C., or an increase in temperature greater than any one of these values. The rejuvenation step involves flowing a rejuvenation gas including $H_2$ over the synthesis catalyst, and may involve a temperature of about 200° C. to about 400° C., or any range including and in between any two integers between these two values, preferably about 350° C. The rejuvenation gas may include downstream $H_2$, such as the high purity $H_2$ provided by the hydrogen separation network (e.g., high purity $H_2$ stream 141/341). The rejuvenation gas may include the $O_2$-depleted gas or a portion thereof. Such a rejuvenation step strips off a portion of poisons that may become associated with the synthesis catalyst (e.g., $NH_3$) during the contacting step.

The process may include a periodic synthesis catalyst regeneration step when the synthesis catalyst includes a Fischer-Tropsch catalyst. A person of skill in the art understands it is sometimes desirable to perform a rejuvenation step rather than a regeneration step, or vice versa, and understands when to perform one versus the other. In the periodic synthesis catalyst regeneration step, the contacting step employing the synthesis catalyst to be regenerated is discontinued for the duration of the synthesis catalyst regeneration step. Such synthesis catalyst regeneration is well known in the art and as recommended by synthesis catalysts suppliers for the particular synthesis catalyst to be regenerated. In any of the above embodiments in which the contacting step produces liquid products at reaction conditions, such as with Fischer-Tropsch reactions, the synthesis catalyst regeneration step may involve:

(1) a dewaxing step involving flowing a dewaxing gas including $H_2$ over the synthesis catalyst, (2) an oxidation step involving flowing an oxidation gas over the synthesis catalyst, and (3) a reduction step involving exposing the synthesis catalyst to a reducing gas that includes $H_2$.

The temperature dewaxing step, the oxidation step, and the reduction step may each independently be from about 200° C. to about 400° C., or any range including and in between any two integers between these two values, and preferably is about 350° C. The dewaxing gas and the reducing gas may each independently include the high purity $H_2$ provided by the hydrogen separation network (e.g., high purity $H_2$ stream 141/341), and may each independently include the $O_2$-depleted gas or a portion thereof. The oxidation gas may include one or more of air, $N_2$-diluted air, or the $O_2$-depleted gas or a portion thereof. The dewaxing step typically involves removing (such as breaking down, cracking, and/or solubilizing) synthetic product associated with the synthesis catalyst; the oxidation step typically involves combusting residual hydrocarbons and/or oxygenated hydrocarbons and oxidizes the synthesis catalyst; and the reduction step typically involves reducing the oxidized synthesis catalyst back to its active form.

In embodiments of the synthesis catalyst rejuvenation step or synthesis catalyst regeneration step involving the $O_2$-depleted gas, it may be that the $O_2$-depleted gas is included without substantial cooling. However, depending on the embodiment, it may be that the $O_2$-depleted gas is included after substantial cooling or that the $O_2$-depleted gas is included with substantial heating. "Substantial" as used in regard to heating and cooling refers to a change in temperature of at least about 100° C. or greater. Such cooling and heating may be accomplished by a heat exchanger such as those described herein, as well as methods known to one of skill in the art. When optimizing the temperature, the skilled person is aware that the oxidation step is effective in the range from about 200° C. to about 400° C.

Start-Up/Restart of Process

In any of the above embodiments, it may be that a start-up step precedes the process or follows the catalyst regeneration step. The start-up step may involve any one or more of the procedures described herein regarding FIG. 1 or the procedure described herein in regard to FIG. 2. In addition to or in the alternative to this procedure, the start-up step may involve heating the synthesis catalyst to a reaction temperature.

In some embodiments, heating the synthesis catalyst involves supplying heat from the steam reformed product, the second reformed product, the $O_2$-depleted gas, heated liquid $H_2O$, steam, or combinations of any two or more thereof. In some embodiments, heating the synthesis catalyst to the reaction temperature involves supplying heat from a boiler to the synthesis catalyst. The boiler may provide heated liquid $H_2O$, steam, or both. Such boilers include, but are not limited to, natural gas or propane-fired boilers, hydrocarbon fueled boilers, electric boilers, and the like.

In embodiments involving a boiler, the boiler may be configured to perform as a steam drum for a contacting step. A person of skill in the art understands the makeup and how to utilize a steam drum. The steam drum is configured to adjust the pressure of the heat exchange fluid where the heat exchange fluid includes phase change between water and steam. By controlling the pressure within each heat exchange conduit, the temperature within each heat exchange conduit may be controlled. For example, the process may include first establishing a pressure in the steam drum with water/steam in equilibrium followed by circulating the water as the heat exchange fluid to the contacting step. As the production of the synthetic product and tail gas occurs in the contacting step, the heat exchange fluid is heated and/or fully or partially vaporized and the heat exchange fluid is eventually returned to the steam drum.

Protective Coatings for Use with the Reformed Products Prior to Cooling

As illustrated in FIG. 1, steam reformed product 115 is directed to the heat exchanger 240 where it is cooled such that water can be removed via water separation unit 201 to provide syngas 117. Similarly, in FIG. 2, ATR product 315 is directed to the heat exchanger 440 where it is cooled. Prior to cooling, such warm reformed products may cause metal dusting corrosion of the conduits. This is especially true for nickel and/or iron bearing metals or metal alloys.

In any of the embodiments described herein, the conduit that includes the reformed product may include an interior side disposed toward the reformed product, where the interior side includes a protective coating. Such protective coatings include, but are not limited to, those described in International Publication WO 2012/054455 A2, incorporated herein by reference in its entirety for any and all purposes. The protective coating may include at least one of a metal oxide or a metal. Such metals may include Cu, Cr, Al, Ag, Au, or combinations of any two or more thereof, or carbides of metals. Such combinations of metals include alloys. Accordingly, the protective coating may include a metal alloy, such as Al—Cu, Al—Ag, Al—Cr, and Cu—Cr alloys. Use of an Al-containing alloy may provide for formation of an alumina scale on the interior surface in contact with the CO, thus providing an additional layer. Metal oxides include oxides of Al and Al-containing alloys. Alumina is a representative oxide of Al. In any of the above embodiments and aspects, the protective coating may include two or more layers.

The protective coating may include at least a first layer in contact with the interior side of the conduit and a second layer in contact with the first layer, where the first layer includes a metal oxide and the second layer includes a metal. In any of the above embodiments, the protective coating may include a first layer in contact with the interior side of the conduit, a second layer in contact with the first layer, and a third layer in contact with the second layer but not the first, where the first layer includes a metal oxide, the second layer includes a metal, and the third layer includes a metal oxide. The metal oxide of the first and third layers may or may not be the same metal oxide. For example, in a preferred embodiment, the first layer may be alumina, the second layer may be an Al-containing alloy (e.g., Cu—Al alloy), and the third layer may be alumina. Further, in any of the above embodiments, it may be that the protective coating includes more than three layers, where each layer may independently be a metal oxide or a metal. In a preferred embodiment, the conduit that includes the reformed product and the interior side disposed toward the reformed product is constructed from a material that includes a high nickel (>30 wt %) alloy material. Suitable high nickel alloy materials may include Alloy 617, Inconel, or other alloys commonly known as "superalloys." The heat exchanger may include one or more heat exchanger walls with a multi-layer protective coating, in which one of the layers includes a metal aluminide, and another of the layers includes an alumina scale grown from the metal aluminide layer using a heat treatment step. The multi-layer protective coating may preferably include a metal aluminide layer, alumina scale layer, a Cu—Al alloy layer, and a second alumina scale layer.

Ethylene Synthesis According to the Present Technology

Figure 3:
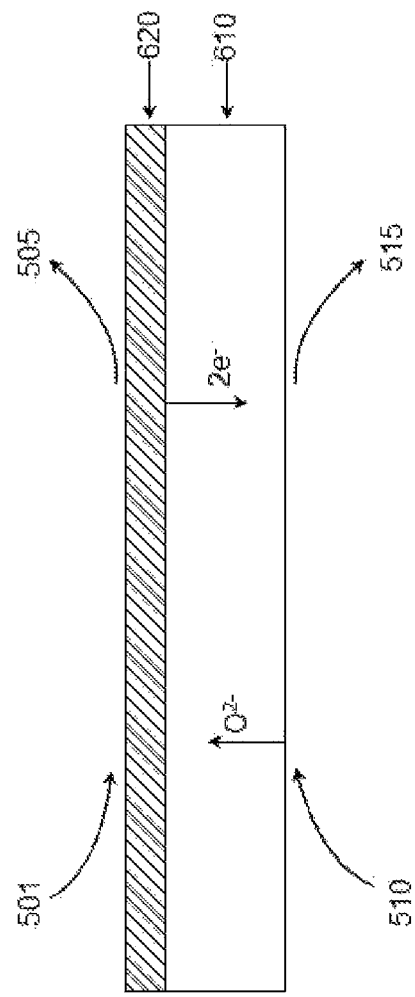
FIG. 3 provides a schematic representation of a process involving forming ethylene, according to several embodiments.

The present technology also provides a process that involves forming ethylene by flowing a reactant feed comprising $CH_4$ over a viral-templated coupling catalyst disposed on the permeate side of an ion transport membrane and flowing an $O_2$-containing gas over a retentate side of the ion transport membrane. FIG. 3 provides an exemplary schematic of a process that involves forming ethylene according to the present technology.

In FIG. 3, reactant feed 501 flows over viral-templated coupling catalyst 620 disposed on a permeate side of ion transport membrane 610. In this illustration, viral-templated coupling catalyst 620 is disposed on the surface of the permeate side of ion transport membrane 610. In the present technology, how the viral-templated coupling catalyst is disposed on the permeate side may include, but is not limited to, an independent layer of the viral-templated coupling catalyst that resides on the permeate side, an independent layer of the viral-templated coupling catalyst that is dispersed on the permeate side, an independent layer of the viral-templated coupling catalyst wherein a portion of the viral-templated coupling catalyst is chemically bonded to the permeate side of the ion transport membrane, or the viral-templated coupling catalyst is integral with the permeate side of the ion transport membrane and forms a layer within the ion transport membrane. Viral-templated coupling catalyst 620 may be a layer from about 1 micrometer (μm) to about 1 millimeter (mm), preferably from about 10 μm to about 50 μm.

Similar to the steam reforming process of the present technology, flowing $O_2$-containing gas 510 over the retentate side of ion transport membrane 610 produces $O_2$-depleted gas 515 by net permeation of oxygen through ion transport membrane 610. This introduces the oxygen to the permeate side of ion transport membrane 610 and allows reactant feed 501 to react via viral-templated coupling catalyst 620 to provide ethylene formation product 505. Ethylene formation product 505 includes ethylene, but also may include $C_2$+ hydrocarbons (e.g., ethane, acetylene, propane, propene, etc.), oxygenated hydrocarbons (e.g., acetic acid), CO, $CO_2$, $H_2O$, or combinations of any two or more thereof. Separation of ethylene from the other potential components of the ethylene formation product may be accomplished by variety of methods known to one skilled in the art, including those methods described in International Publication WO 2008/150451 A2, incorporated herein by reference in its entirety for any and all purposes. Separation of the ethylene formation product may provide an ethylene formation tail gas (an "EF tail gas"), where the EF tail gas may include one or more of $CH_4$, CO, $CO_2$, or $H_2O$. The EF tail gas may be directed to the steam reforming process, either directly combined with reformer feed as a reclamation stream or fed to the $CO_2$ recovery step. Thus, the process involving forming ethylene may further provide more $CO_2$ and/or $H_2$ for the previously described steam reforming process increasing the overall carbon efficiency of the combined processes in an integrated facility. Moreover, the process that involves forming ethylene may provide heat to the previously described steam reforming process, where the heat may be radiant heat.

Ion transport membrane 610 may be a variety of shapes, such as tubes or plates. In the process involving forming ethylene, the ion transport membrane may be a tube. In such embodiments, the permeate side may be the interior of the tube and the retentate side may be the exterior of the tube.

In the process involving forming ethylene, the $O_2$-depleted gas may be at a temperature of about 600° C. to about 1,200° C., or any range including and in between any integer between these two values. In any of the above embodiments, the $O_2$-depleted gas may be about 0% to about 20% $O_2$ on a molar basis, or any range including and in between any two integers between these two values.

It is to be understood that the flow of the reactant feed may be co-current, counter-current, or cross-current to the flow of the $O_2$-containing gas. The $O_2$-containing gas may include air or air enriched with $O_2$. The $O_2$-containing gas may be about 0.1% to about 50% $O_2$ on a molar basis, or any range including and in between any integer between these two values. The $O_2$-containing gas may be at a pressure from about 20 psig to about 500 psig, or any range including and in between any integer between these two values.

The viral-templated coupling catalysts are known in the art, as illustrated by U.S. Pat. No. 8,436,506 and U.S. Pat. Publ. 2014/0048126. For example, genetically engineered M13 bacteriophages may be employed to generate a porous template for the deposition of inorganic materials by a covalent layer-by-layer assembly method that uses a cross-linker (e.g., a carbodiimide) employed in bioconjugation. Organizing these bacteriophages into a three-dimensional network generates a porous scaffold for the assembly of metallic nanoparticles, crystals, and/or metal oxides into nanowire networks. Such viral-templated catalysts may include at least one oxide of Cu, Cr, Ga, Fe, Ag, Pd, Zn, Zr, Mn, Mo, V, Ce, Al, a rare earth metal, or a combination of any two or more thereof as an oxide. The viral template catalyst may therefore include at least one oxide of Cu, Pd, Ga, Sc, Y, Zr, In, Nd, Eu, Sm, Ce, Gd, Hf, Ho, Tm, W, La, Dy, In, S, Zn, Yb, Ni, Lu, Ta, P, Pt, Bi, Sn, Nb, Sb, Ge, Ag, Au, Pb, Re, Fe, Al, Tl, Pr, Co, Rh, Ti, V, Cr, Mn, Ir, As, Tb, Er, Te, Mo, or a combination of any two or more thereof as an oxide, and may further include at least one of an alkali metal, an alkali earth metal, or boron. In any of the above embodiments involving forming ethylene, the viral-templated coupling catalyst may include a manganese oxide; at least one alkali metal, alkali earth metal, or boron; and at least one of Ga, Sc, Y, Zr, In, Nd, Eu, Sm, Ce, Gd, Hf, Ho, Tm, W, La, Dy, In, S, Zn, Yb, Ni, Lu, Ta, P, Pt, Bi, Sn, Nb, Sb, Ge, Ag, Au, Pb, Re, Fe, Al, Tl, Pr, Co, Rh, Ti, V, Cr, Mn, Ir, As, Tb, Er, Te or Mo. In such embodiments, the viral-templated coupling catalyst may include a manganese oxide, an alkali metal, tungsten, and niobium, on a silica support. In any of the above embodiments involving forming ethylene, the viral-templated coupling catalyst may be disposed on the surface of the ion transport membrane on the permeate side.

In any of the above embodiments, forming ethylene may be performed at a temperature of about 400° C. to about 1,000° C., or any range including and in between any integer between these two values. As an example, forming ethylene may be performed at a temperature of about 400° C. to about 800° C.

In any of the above embodiments involving forming ethylene, the reactant feed may be at a pressure falling in the range of about 1 atm to about 20 atm, or any range including and in between any integer between these two values. The partial pressure of methane in the reactant feed may fall in the range of about 0.1 atm to about 20 atm, or any range including and in between any tenth of an integer between these two values. The GSHV of the methane feed may fall in the range of about 20,000 $hr^{-1}$ to about 5,000,000 $hr^{-1}$.

In any of the above embodiments involving forming ethylene, the product produced at least includes ethylene (the "ethylene formation product"). The ethylene formation product may further include $CH_4$ (unreacted in the reactant feed), $C_2$+ hydrocarbons (e.g., ethane, acetylene, propane, propene, etc.), oxygenated hydrocarbons (e.g., acetic acid), CO, $CO_2$, $H_2O$, or combinations of any two or more thereof. In any of the above embodiments involving forming ethylene, it may be the process further involves contacting the ethylene formation product with a synthesis catalyst to produce a synthetic product. The synthetic product may include one or more compounds selected from $C_1$ to $C_{100}$ hydrocarbons, $C_1$ to $C_{100}$ oxygenated hydrocarbons, or a combination thereof. In such embodiments, the synthesis catalyst may include an ethylene oxide production catalyst, a dimethoxyethane production catalyst, a vinyl acetate monomer production catalyst, or a combination of any two or more thereof.

Ethylene may be used to produce vinyl acetate monomer (VAM), where such production of VAM may include a VAM catalyst. The VAM catalyst may include Pd, Au, and potassium acetate (KOAc). The VAM catalysts preferably contain a refractory support, such as silica, silica-alumina, titania, or zirconia. In any of the above embodiments, the catalyst may include more than about 2 wt % Pd, more than about 4 wt % Pd, more than about 10 wt % Pd and in some embodiments, at least about 12 wt % Pd. In VAM production, the feed in the contacting step may include ethylene, acetic acid, and $O_2$. The initial molar ratio of ethylene to acetic acid to $O_2$ in the contacting step (i.e., before reaction) may be in the range from about 6:3:1 to about 2:2:1.

Synthesis Catalysts of the Present Technology

A person of ordinary skill in the art will be familiar with synthesis catalysts suitable for performing different synthetic reactions.

For example, in embodiments of the process where the synthetic reaction involves a Fischer-Tropsch (FT) process, the synthesis catalyst includes a FT catalyst and the tail gas includes an FT tail gas. FT catalysts may include cobalt or iron, and may further include a promoter such as Cu, Mn, Pd, Pt, Rh, Ru, Re, Ir, Au, Ag, Os, or a combination of any two or more thereof. For example, the FT catalyst may include FeCuMn. The FT catalyst may also include a support material. Suitable support materials include a refractory metal oxide, carbide, carbon, nitride or a mixture of any two or more thereof. The FT catalyst may further include a surface modified support material, wherein the surface of the support has been modified by being treated with silica, titania, zirconia, magnesia, chromia, alumina, or a mixture of any two or more thereof. In any of the above embodiments, the support material may include alumina, zirconia, silica, titania, or a mixture of two or more thereof. In some embodiments, the support material may include a $TiO_2$ modified silica. In any of the above embodiments, the surface of the surface-modified support material may be amorphous. In any of the aspects and embodiments described herein, it may be that the FT catalyst includes a graded catalyst.

Where the synthetic reaction involves methanol production, the synthetic catalyst may include a copper-based catalyst such as Cu/ZnO/Al$_2$O$_3$ and the tail gas may include a methanol production-derived tail gas.

Where the synthetic reaction involves higher alcohol production (a "higher alcohol" being a C$_2$+ alcohol), the synthetic catalyst may include a higher alcohol synthesis catalyst. The higher alcohol synthesis catalyst may include any one or more catalysts as described in Li, D. et al. *Fuel Processing Technology*, 2007, 88, 125-127; Xiang, M. et al. *Catalysis Communications*, 2007, 8, 503-507; Xiang, M. et al. *Fuel*, 2008, 87, 599-603; U.S. Pat. No. 7,858,667, the references cited in each therein, or a combination of any two or more thereof. For example, the higher alcohol synthesis catalyst may be a Mo$_2$C-based catalyst such as a K/Ni/β-Mo$_2$C catalyst optionally with a molar ratio for Ni to Mo of about 1:6 to about 1:8, a K/Co/β-Mo$_2$C catalyst optionally with a molar ratio for Co to Mo of about 1:6 to about 1:8, or a K/Fe/β-Mo$_2$C catalyst optionally with a molar ratio for Fe to Mo of about 1:6 to about 1:8; a Pd—Zn based catalyst such as a Pd—Zn alloy dispersed on alumina, optionally in combination with an FT catalyst; or a combination of any two or more thereof Where the synthetic reaction involves ethylene oxide ("EO") production, the synthetic catalyst may include a metal, a metal oxide, or a mixed metal oxide of Ag, Mo, W, V, Nb, Sb, Sn, Pt, Pd, Cs, Zr, Cr, Mg, Mn, Ni, Co, Ce, or a mixture of any two or more thereof. These EO synthesis catalysts may also include one or more alkali metals or alkaline earth metals or other transition metals, rare earth metals or lanthanides. Elements such as P and Bi may be present. The EO synthesis catalyst may be supported. Useful support materials include, but are not limited to, metal oxides (e.g., alumina, titania, zirconia), silica, mesoporous materials, zeolites, refractory materials, or combinations of any two or more thereof. In particular, the EO synthesis catalyst may be any one of the catalysts disclosed in U.S. Pat. No. 5,597,773, U.S. Pat. No. 5,703,253, U.S. Pat. No. 5,705,661, U.S. Pat. No. 6,762,311, and European Pat. 0266015, each of which is incorporated herein by reference in its entirety for any and all purposes. In EO production, ethylene oxide is generally produced by the oxidation of ethylene over an EO catalyst, where the feed in the contacting step will include a mixture of ethylene and oxygen. The molar ratio of ethylene to oxygen may be less than about 4:1, or less than about 3:1. The molar ratio of ethylene to oxygen may be in the range from 0.2:1 to about 4:1, or from about 0.5:1 to about 3:1, or from about 1:1 to about 3:1. In such embodiments involving EO production, the tail gas may include an EO production-derived tail gas.

Where the synthetic reaction involves DME production, the synthetic catalyst may include a blend of a methanol synthesis catalyst, such as Cu/ZnO/Al$_2$O$_3$, and a dehydration catalyst, such as γ-Al$_2$O$_3$. In such embodiments involving DME production, the tail gas may include a DME production-derived tail gas.

The synthetic product and/or the ethylene of the process involving forming ethylene may further be reacted to provide a desired product.

For example, the synthetic product may be directed to a hydrocracking reaction. Hydrocracking catalysts suitable for such reactions may include zeolite catalysts. Zeolite catalysts include, but are not limited to, beta zeolite, omega zeolite, L-zeolite, ZSM-5 zeolites and Y-type zeolites. The hydrocracking catalyst may also include one or more pillared clays, MCM-41, MCM-48, HMS, or a combination of any two or more thereof. The hydrocracking catalyst may include Pt, Pd, Ni, Co, Mo, W, or a combination of any two or more thereof. The hydrocracking catalyst may further include a refractory inorganic oxide such as alumina, magnesia, silica, titania, zirconia, silica-alumina, or combinations of any two or more thereof. The hydrocracking catalyst may further include a hydrogenation component. Examples of suitable hydrogenation components include, but are not limited to, metals of Group IVB and Group VIII of the Periodic Table and compounds of such metals. For example, molybdenum, tungsten, chromium, iron, cobalt, nickel, platinum, palladium, iridium, osmium, rhodium, ruthenium, or combinations of any two or more thereof may be used as the hydrogenation component. Exemplary catalysts are described in U.S. Pat. No. 6,312,586, which is incorporated herein by reference in its entirety for any and all purposes.

The synthetic product may be directed to a hydrotreating, where the hydrotreating involves a hydrotreating catalyst. The hydrotreating catalyst may include Ni, Mo, Co, W, or combinations of any two or more thereof. The hydrotreating catalyst may be a supported catalyst, such as a hydrotreating catalyst supported on alumina. In some embodiments, the catalyst may include Mo—W/Al$_2$O$_3$.

It may be that the synthetic product is directed to a hydrocarbon oxidation involving an oxidation catalyst. The oxidation catalyst may include a metal, metal oxide, or mixed metal oxide of Mo, W, V, Nb, Sb, Sn, Pt, Pd, Cs, Zr, Cr, Mg, Mn, Ni, Co, Ce, or a combination of any two or more thereof. These catalysts may further include one or more alkali metals or alkaline earth metals or other transition metals, rare earth metals or lanthanides. Elements such as P and Bi may be present. The catalyst may be supported and, if so, useful support materials include metal oxides (e.g. alumina, titania, zirconia), silica, mesoporous materials, zeolites, refractory materials, or combinations of two or more thereof.

In any of the aspects and embodiments described herein, it may be that after contacting the synthesis catalyst, the resulting synthetic product is directed to a hydrocracking, hydrotreating, or combination thereof. For example, the first synthesis catalyst may be a FT catalyst to produce a FT product, where the FT product is subsequently contacted with a hydrotreating catalyst to product a hydrotreated product. It may be the hydrotreated product is then contacted with a hydrocracking catalyst to produce a hydrocracked product.

Microchannel Processes According to the Present Technology

In any of the aspects and embodiments described herein, the contacting step may involve flowing the H$_2$ and CO through a microchannel reactor that includes the synthesis catalyst to produce the synthetic product. In such embodiments, the microchannel reactor may include at least one process microchannel in thermal communication with a heat exchange microchannel, the synthesis catalyst is disposed within the process microchannel.

In any of the embodiments described herein, the steam reforming step may involve flowing the first reforming feed through a microchannel reactor that includes a steam reforming catalyst to produce the steam reformed product. In such embodiments, the microchannel reactor may include at least one process microchannel in thermal communication with a heat exchange microchannel, the steam reforming catalyst is disposed within the process microchannel. In any of the embodiments described herein, the second reforming may involve flowing the second reforming feed through a microchannel reactor that includes the second reforming catalyst to produce the second reformed product. In such embodiments, the microchannel reactor may include at least one process microchannel in thermal communication with a heat exchange microchannel, the second reforming catalyst is disposed within the process microchannel.

In any of the above embodiments, the heat exchange microchannel includes a heat exchange fluid, where the process involves flowing the heat exchange fluid through the heat exchange microchannel. The synthesis catalyst and/or steam reforming catalyst may be disposed on interior walls of the process microchannels. Where the synthesis catalyst and/or steam reforming catalyst are within a process microchannel, the synthesis catalyst or steam reforming catalyst may be used as a particulate solid loaded into the process channels, coated on interior walls of the process microchannels, and/or grown on interior walls of the process microchannels. The synthesis catalyst and/or steam reforming catalyst may be supported on a support having a flow-by configuration, a flow-through configuration, or a serpentine configuration. The synthesis catalyst and/or steam reforming catalyst may be supported on a support having the configuration of a foam, felt, wad, fin or a combination of two or more thereof. Alternatively, the synthesis catalyst and/or steam reforming catalyst may be in the form of insert which may be fitted within a suitable slot within the reactor.

In any of the aspects and embodiments described herein, it may be that the deactivation rate of the synthesis catalyst in the process microchannel is less than a loss of about 0.2% CO conversion per day. In any of the aspects and embodiments described herein, it may be that the synthesis catalyst includes a graded catalyst. A "graded catalyst" refers to a catalyst with one or more gradients of catalytic activity. The graded catalyst may have a varying concentration or surface area of a catalytically active metal. The graded catalyst may have a varying turnover rate of catalytically active sites. The graded catalyst may have physical properties and/or a form that varies as a function of distance. For example, the graded catalyst may have an active metal concentration that is relatively low at the entrance to a process microchannel and increases to a higher concentration near the exit of the process microchannel, or vice versa; or a lower concentration of catalytically active metal nearer the center (i.e., midpoint) of a process microchannel and a higher concentration nearer a process microchannel wall, or vice versa.

Process microchannels may include internal surface features configured to impart a disruptive flow when flowing the $H_2$ and CO in the microchannel reactor. The microchannel reactor may further include a plurality of process microchannels and a plurality of heat exchange microchannels, the synthesis catalyst is disposed in the process microchannels, each heat exchange microchannel being in thermal communication with at least one process microchannel, at least one manifold for flowing the $H_2$ and CO into the process microchannels, at least one manifold for flowing synthetic product out of the process microchannels, at least one manifold for flowing a heat exchange fluid into the heat exchange microchannels, and at least one manifold for flowing the heat exchange fluid out of the heat exchange microchannels. The flow in the process microchannel may be co-current, counter-current, or cross-current to the flow in the heat exchange channel.

In any of the embodiments including process microchannels, the process microchannel may include at least one heat transfer wall and the heat flux for heat exchange within the microchannel reactor is in the range from about 0.05 to about 200 watts per square centimeter of surface area of the at least one heat transfer wall. The heat flux may also be from about 0.1 to about 10 $W/cm^2$, or from about 1 to about 10 $W/cm^2$, or from about 1 to about 8 $W/cm^2$, or from about 1 to about 5 $W/cm^2$.

The pressure in the microchannel may be up to about 50 atm. The pressure in the microchannel may be about 5 atm, about 10 atm, about 15 atm, about 20 atm, about 25 atm, about 30 atm, about 35 atm, about 40 atm, about 45 atm, about 50 atm, or any range including and in between any two of these values. The temperature in the process microchannel may be of about 150° C. to about 400° C. Where the synthesis catalyst in the process microchannel is an FT catalyst, the temperature in the process microchannel with the FT catalyst may be from about 150° C. to about 300° C. The temperature in the process microchannel with the FT catalyst may be about 150° C., about 160° C., about 170° C., about 180° C., about 190° C., about 200° C., about 210° C., about 220° C., about 230° C., about 240° C., about 250° C., about 260° C., about 270° C., about 280° C., about 290° C., about 300° C., or any range including and in between any two of these values.

The gas hourly space velocity (GHSV) for the flow of fluids in any of the microchannels may be at least about 500 $hr^{-1}$, for example, the GSHV in any of the microchannels may be in the range from about 500 $hr^{-1}$ to about 100,000 $hr^{-1}$. The GSHV in the process microchannel may be at least about 500 $hr^{-1}$. For example, the GSHV in the process microchannel may be about 500 $hr^{-1}$ to about 100,000 $hr^{-1}$.

The contact time of the $H_2$ and CO with the synthesis catalyst or the steam reforming feed with a steam reforming catalyst in the process microchannels may range from about 30 to about 2000 milliseconds (ms). The contact time with the synthesis catalyst in the process microchannels may be from about 30 ms to about 1,000 ms, or from about 30 ms to about 500 ms, or from about 30 ms to about 250 ms, or from about 30 ms to about 100 ms.

Modular Processes According to the Present Technology

In any of the aspects and embodiments described herein, it may be a the steam reforming step is carried out within a reforming enclosure and the contacting step is carried out in a synthesis enclosure. It may be that at least one steam reforming step and at least one second reforming step are carried out in the reforming enclosure. In such embodiments, it may be that a reformer train includes one or more reforming enclosures, wherein at least one steam reforming step is carried out in at least one reforming enclosure. For example, reforming enclosure 290 of FIG. 1 includes a steam reforming step as well as a combustion step; reforming enclosure 490 of FIG. 2 includes a steam reforming step and a subsequent autothermal reforming step. The reformer train may include a plurality of reforming enclosures. Each reforming enclosure may perform a different reforming reaction. For example, one reforming enclosure may perform autothermal reforming while another may perform the steam reforming step. Similarly, each synthesis enclosure may perform a different synthesis reaction through inclusion of different synthesis catalysts. In any of the above embodiments, the reformer train may be in controlled flow communication with the synthesis enclosure.

The process may involve a periodic synthesis catalyst regeneration step where the controlled flow communication is discontinued for the duration of the synthesis catalyst regeneration step. The process may involve a periodic synthesis catalyst rejuvenation step where the controlled flow communication is discontinued for the duration of the synthesis catalyst rejuvenation step.

In any of the above embodiments involving a reforming enclosure and a synthesis enclosure, the process may further involve a start-up step following the synthesis catalyst regeneration step. The start-up step may include any one of the optional start-up processes described in FIGS. 1 and 2, and/or may include heating the catalyst to a reaction temperature. In such embodiments, heating the catalyst to the reaction temperature may involve supplying heat from a boiler. The boiler may be configured as steam drum for a contacting step.

In any of the above embodiments, heating the catalyst to a reaction temperature may involve heating the catalyst of the synthesis enclosure, wherein heating the catalyst of the synthesis enclosure involves supplying heat from at least a second synthesis enclosure, at least one reforming enclosure, at least one reformer train, or a combination of any two or more thereof. In any of the above embodiments, the heating the catalyst of the synthesis enclosure may involve supplying heat from at least one reforming enclosure.

In any of the above embodiments, heating the synthesis catalyst of the synthesis enclosure may involve supplying heat from at least one reformer train. Such heat may come from an $O_2$-depleted gas. The heat may be transferred via a heat exchanger as described herein, such as where the synthesis catalyst is in a process microchannel in thermal communication with a heat exchange microchannel and the heat exchange microchannel includes an $O_2$-depleted gas from a reformer train. In any of the above embodiments, it may be that heating the catalyst of the synthesis enclosure involves supplying heat to a boiler and subsequently supplying heat from the boiler to the catalyst of the synthesis enclosure.

III. Conclusion

The present technology is not to be limited in terms of the particular figures described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, or labeled compounds, which can, of course, vary. It is also to be understood that the terminology used herein is for the purpose of describing particular aspects only, and is not intended to be limiting.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology includes, but is not limited to, the following lettered paragraphs:

A. A process comprising
  steam reforming a first reforming feed to produce a steam reformed product comprising $H_2$ and CO ("the steam reforming step");
  optionally subjecting a second reforming feed comprising the steam reformed product to a second reforming step to provide a second reformed product comprising $H_2$ and CO; and
  contacting the $H_2$ and CO with a synthesis catalyst to produce a synthetic product and a tail gas ("the contacting step");
  wherein
    the synthetic product comprises one or more compounds selected from $C_1$ to $C_{100}$ hydrocarbons, $C_1$ to $C_{100}$ oxygenated hydrocarbons, or a combination thereof;
    the first reforming feed comprises $CH_4$; and
    the first and/or the second reforming feed comprises one or more of
      $CO_2$ separated from the steam reformed product and/or the second reformed product,
      $CO_2$ separated from the tail gas, or
      $CO_2$ formed from subjecting at least a portion of the tail gas to a water-gas shift ("WGS") reaction which forms a WGS product comprising $CO_2$ and $H_2$;
    heat for the steam reforming step is provided by combustion and optionally partial oxidation;
    the combustion and optional partial oxidation comprises flowing a combustion gas comprising $H_2$ over a permeate surface of an ion transport membrane and flowing an $O_2$-containing gas over a retentate surface of an ion transport membrane to react the combustion gas, produce heat, and produce an exhaust gas comprising $H_2O$ ("the combustion step").

B. The process of Paragraph A, wherein the combustion gas comprises one or more of
  $H_2$ separated from the steam reformed product and/or the second reformed product,
  $H_2$ separated from the tail gas, or
  $H_2$ formed from subjecting at least a portion of the tail gas to the WGS reaction.

C. The process of Paragraph A or Paragraph B, wherein the combustion step is carried out in the presence of a combustion catalyst.

D. The process of any one of Paragraphs A-C, wherein the first reforming feed comprises the exhaust gas.

E. The process of any one of Paragraphs A-D, wherein the second reforming feed comprises the exhaust gas.

F. There process of any one of Paragraphs A-E, wherein flowing the $O_2$-containing gas over the retentate surface in the combustion step produces an $O_2$-depleted gas.

G. The process of any one of Paragraphs A-F, wherein the contacting step produces the synthetic product, the tail gas, and $H_2O$.

H. The process of Paragraph G, wherein $H_2O$ produced in the contacting step is separated from the synthetic product and the tail gas.

I. The process of any one of Paragraphs A-H, wherein the WGS reaction comprises a portion of $H_2O$ from the steam reformed product, a portion of $H_2O$ from the second reformed product, a portion of $H_2O$ produced in the contacting step, or a combination of any two or more thereof.

J. The process of any one of Paragraphs A-I, wherein the synthesis catalyst comprises a Fischer-Tropsch catalyst, a methanol production catalyst, a higher alcohol synthesis catalyst, or a combination of any two or more thereof.

K. The process of any one of Paragraphs A-J, wherein the initial mole ratio of $H_2$ to CO fed to the contacting step is in the range from about 0.5:1 to about 4:1.

L. The process of any one of Paragraphs A-K, wherein the combustion gas further comprises at least one of
  $CO_2$ separated from the steam reformed product and/or the second reformed product,
  $CO_2$ separated from the tail gas, or
  $CO_2$ formed from subjecting at least a portion of the tail gas to a WGS reaction.

M. The process of any one of Paragraphs A-L, wherein the steam reformed product is purified prior to the optional second reforming step or the contacting step.

N. The process of Paragraph M, wherein purifying the steam reformed product comprises adding CO provided by a hydrogen separation network.

O. The process of Paragraph M and Paragraph N, wherein purifying the steam reformed product comprises removing $CO_2$ by a $CO_2$ separation network.

P. The process of any one of Paragraphs M-O, wherein purifying the steam reformed product comprises adding the WGS product.

Q. The process of any one of Paragraphs M-P, wherein purifying the steam reformed product comprises adding CO separated from the WGS product by a hydrogen separation network.

R. The process of any one of Paragraphs A-Q, wherein the steam reformed product comprises $H_2O$ and purifying the steam reformed product comprises separating the $H_2O$ from the steam reformed product.

S. The process of any one of Paragraphs A-R, further comprising contacting the synthetic product with a hydrocracking catalyst, a hydrotreating catalyst, a hydrocarbon oxidation catalyst, or a combination of any two or more thereof.

T. The process of any one of Paragraphs A-S, further comprising
  combining the steam reformed product with the product of a partial oxidation process, an autothermal reforming process, a $CO_2$ reforming process, a coal gasification process, or combinations of any two or more thereof to produce a combined feed; and
  contacting the combined feed with the synthesis catalyst to produce the synthetic product.

U. The process of any one of Paragraphs A-T, wherein the process comprises subjecting the steam reformed product to a second reforming step to produce a second reformed product comprising $H_2$ and CO.

V. The process of Paragraph U, wherein the second reforming step comprises partial oxidation, autothermal reforming, $CO_2$ reforming, steam reforming, reverse water gas shift, or combinations of any two or more thereof.

W. The process of any one of Paragraphs A-V, wherein at least the second reforming feed comprises one or more of
  $CO_2$ separated from the steam reformed product and/or the second reformed product,
  $CO_2$ separated from the tail gas, or
  $CO_2$ formed from subjecting at least a portion of the tail gas to the WGS reaction.

X. The process of any one of Paragraphs A-W, wherein at least the second reforming feed comprises one or more of
  $H_2$ separated from the steam reformed product and/or the second reformed product, or
  $H_2$ formed from subjecting at least a portion of the tail gas to the WGS reaction.

Y. The process of any one of Paragraphs A-C and F-X, wherein the second reforming step comprises the combustion step.

Z. The process of Paragraph Y, wherein the combustion step occurs in a combustion zone followed by the second reforming step in a reforming zone.

AA. The process of any one of Paragraphs A-C and F-Z, wherein
  the second reforming step is an autothermal reforming step comprising the combustion step;
  the second reforming feed comprises the combustion gas;
  an autothermal reforming ion transport membrane (ATR-ITM) comprises the ion transport membrane of the combustion step;
  the second reformed product comprises the exhaust gas; and
  the first reforming feed and second reforming feed do not comprise the exhaust gas.

AB. The process of Paragraph AA, wherein the autothermal reforming comprises flowing the second reforming feed over a permeate surface of the ATR-ITM and flowing the $O_2$-containing gas over a retentate surface of the ATR-ITM to produce the reformed product.

AC. The process of any one of Paragraphs A-AB, wherein the steam reforming comprises a steam reforming catalyst, wherein the steam reforming catalyst comprises Ni, Ru, Rh, Pd, Ir, Pt, or a combination of any two or more thereof.

AD. The process of Paragraph AC, wherein the steam reforming catalyst further comprises at least one of Au, Ag, Sn, Cu, Co, Mo, Fe, Gd, or B.

AE. The process of any one of Paragraphs A-AD, further comprising flowing the steam reformed product and/or the second reformed product through a heat exchanger to lower the temperature of the steam reformed product prior to the second reforming step or the contacting step.

AF. The process of Paragraph AE, wherein flowing the steam reformed product through a heat exchanger comprises
  flowing the steam reformed product and/or the second reformed product through a first conduit; and
  flowing a heat exchange fluid through a second conduit;
  wherein the steam reformed product and heat exchange fluid are in thermal communication.

AG. The process of Paragraph AF, wherein the heat exchange fluid comprises air, the $O_2$-containing gas, water, or a combination of any two or more thereof.

AH. The process of Paragraph AF or Paragraph AG, wherein the heat exchange fluid comprises water;
flowing the steam reformed product and/or the second reformed product through the heat exchanger further comprises generating steam from the heat exchange fluid; and
the first reforming feed further comprises the steam from the heat exchange fluid.

AI. The process of any one of Paragraphs AE-AH, wherein flowing the steam reformed product through a heat exchanger comprises
flowing the steam reformed product and/or the second reformed product through a first conduit;
flowing a first heat exchange fluid through a second conduit; and
flowing a second heat exchange fluid through a third conduit;
wherein the steam reformed product and at least one of the first heat exchange fluid or the second heat exchange fluid are in thermal communication.

AJ. The process of any one of Paragraphs AF-AI, wherein
the steam reformed product and/or the second reformed product comprises $H_2O$; and
the $H_2O$ is separated from the steam reformed product subsequent to flowing the steam reformed product through the heat exchanger.

AK. The process of any one of Paragraphs AF-AJ, wherein the first conduit comprises a interior side disposed toward the steam reformed product, wherein the interior side comprises a protective coating.

AL. The process of Paragraph AK, wherein the protective coating comprises at least one of a metal oxide, a metal aluminide, or a metal alloy.

AM. The process of Paragraph AK or Paragraph AL, wherein the protective coating comprises two or more layers.

AN. The process of any one of Paragraphs AK-AM, wherein the protective coating comprises at least a first layer in contact with the interior side of the conduit and a second layer in contact with the first layer; the first layer comprises a metal oxide; and the second layer comprises a metal alloy.

AO. The process of any one of Paragraphs AL-AN, wherein the metal oxide comprises alumina.

AP. The process of any one of Paragraphs AL-AO, wherein the metal alloy comprises an Al-containing alloy.

AQ. The process of any one of Paragraphs A-AP, further comprising including a portion of the tail gas with the $H_2$ and CO in the contacting step, recycling a portion of the tail gas to the steam reforming step, and/or recycling a portion of the tail gas to the second reforming step.

AR. The process of any one of Paragraphs A-AQ, wherein the process comprises purifying the portion of the tail gas prior to recycling it to the steam reforming step, recycling it to the second reforming step, and/or including it in the contacting step.

AS. The process of Paragraph AR, wherein purifying the portion of the tail gas involves separating $H_2$ from the tail gas by a $H_2$ separation network and/or removing $CO_2$ from the tail gas by a $CO_2$ separation network.

AT. The process of any one of Paragraphs A-AS, comprising flowing the tail gas and/or portion of the tail gas through a heat exchanger to raise the temperature of the tail gas prior to subjecting it to the WGS reaction, recycling the portion of the tail gas to the steam reforming step, recycling the portion of the tail gas to the second reforming step, and/or including the portion of the tail gas in the contacting step.

AU. The process of any one of Paragraphs A-AT, comprising including a portion of the WGS product in the first reforming feed, the second reforming feed, or both.

AV. The process of Paragraph AU, wherein the process further comprises flowing the portion of the WGS product through a heat exchanger to raise the temperature of the WGS product prior to including in the first reforming feed, the second reforming feed, or both.

AW. The process of Paragraph AU or Paragraph AV, wherein flowing the portion of the tail gas and/or the portion of the WGS product through a heat exchanger comprises
flowing the portion of the tail gas and/or the portion of the WGS product through a first conduit; and
flowing a heat exchange fluid through a second conduit;
wherein the portion of tail gas and/or portion of the WGS and heat exchange fluid are in thermal communication.

AX. The process of Paragraph AW, wherein the heat exchange fluid comprises the steam reformed product.

AY. The process of Paragraph AW or Paragraph AX, wherein the heat exchange fluid comprises the second reformed product.

AZ. The process of any one of Paragraphs AW-AY, wherein the heat exchange fluid comprises the $O_2$-containing gas.

BA. The process of any one of Paragraphs AW-AZ, wherein the heat exchange fluid comprises the $O_2$-depleted gas.

BB. The process of any one of Paragraphs AV-BA, wherein flowing the portion of the tail gas and/or the portion of the WGS product through a heat exchanger comprises
flowing the portion of the tail gas and/or the portion of the WGS product through a first conduit;
flowing a first heat exchange fluid through a second conduit; and
flowing a second heat exchange fluid through a third conduit;
wherein the portion of the tail gas and/or the portion of the WGS product and at least one of the first heat exchange fluid or the second heat exchange fluid are in thermal communication.

BC. The process of any one of Paragraphs A-BB, wherein the combustion gas comprises $H_2$ separated from the steam reformed product by a hydrogen separation network.

BD. The process of any one of Paragraphs A-BC, wherein the combustion gas comprises $H_2$ separated from the WGS product.

BE. The process of any one of Paragraphs A-BD, wherein the $O_2$-depleted gas is at a temperature of about 500° C. to about 1,200° C.

BF. The process of any one of Paragraphs A-BE, wherein the synthetic product predominantly comprises one or more compounds selected from $C_1$ to $C_{50}$ hydrocarbons.

BG. The process of Paragraph BF, wherein the synthesis catalyst comprises a Fischer-Tropsch catalyst.

BH. The process of any one of Paragraphs A-BG, wherein the contacting step comprises flowing the $H_2$ and CO through a microchannel reactor comprising the synthesis catalyst to produce the synthetic product.

BI. The process of Paragraph BH, wherein the microchannel reactor comprises at least one process microchannel in thermal communication with a heat exchange microchannel, and the synthesis catalyst is disposed within the process microchannel.

BJ. The process of Paragraph BI, wherein the process microchannel comprises internal surface features configured to impart a disruptive flow when flowing the $H_2$ and CO in the microchannel reactor.

BK. The process of Paragraph BI or Paragraph BJ, wherein the synthesis catalyst comprises one or more of particulate solid catalyst loaded into the process microchannels, an engineered structure disposed within the process microchannels, or a coating disposed on interior walls of the process microchannels.

BL. The process of any one of Paragraphs BH-BK, wherein the microchannel reactor comprises:
- a plurality of process microchannels and a plurality of heat exchange microchannels, wherein the synthesis catalyst is disposed in the process microchannels, and each heat exchange microchannel is in thermal communication with at least one process microchannel,
- at least one manifold for flowing the $H_2$ and CO into the process microchannels,
- at least one manifold for flowing the synthetic product out of the process microchannels,
- at least one manifold for flowing a heat exchange fluid into the heat exchange microchannels, and
- at least one manifold for flowing the heat exchange fluid out of the heat exchange microchannels.

BM. The process of any one of Paragraphs BI-BL, wherein the process microchannel comprises at least one heat transfer wall, and the heat flux for heat exchange within the microchannel reactor is in the range from about 0.5 to about 10 watts per square centimeter of surface area of the at least one heat transfer wall.

BN. The process of any one of Paragraphs A-BM, wherein the steam reforming step is carried out within a reforming enclosure and the contacting step is carried out in a synthesis enclosure.

BO. The process of Paragraph BN, wherein the second reforming step is carried out in the reforming enclosure.

BP. The process of Paragraph BN or Paragraph BO, wherein a reformer train comprises one or more reforming enclosures.

BQ. The process of Paragraph BP, wherein the reformer train comprises a plurality of reforming enclosures.

BR. The process of Paragraph BP or Paragraph BQ, wherein the reformer train is in controlled flow communication with the synthesis enclosure.

BS. The process of any one of Paragraphs A-BR, wherein the process further comprises a start-up step, wherein the start-up step comprises
- utilizing natural gas and/or a start-up fuel as the combustion gas in the combustion step and subsequently performing the steam reforming step;
- upon generation of the steam reformed product or the second reformed product, including the steam reformed product and/or second reformed product in the combustion gas and discontinuing inclusion of natural gas and/or start-up fuel in the combustion gas;
- subsequently including in the combustion gas one or more of
    - $H_2$ separated from the steam reformed product and/or the second reformed product,
    - $H_2$ separated from the tail gas, or
    - $H_2$ formed from subjecting at least a portion of the tail gas to the WGS reaction; followed by
- starting a compressor to provide additional pressure for the contacting step.

BT. The process of Paragraph BS, wherein in the start-up step the steam reformed product and/or second reformed product is purified prior to inclusion in the combustion gas.

BU. The process of Paragraph BS or Paragraph BT, wherein in the start-up step the controlled flow communication is absent prior to the start-up step and instituted subsequent to starting the compressor.

BV. The process of Paragraph BS or Paragraph BT, wherein in the start-up step the controlled flow communication is absent prior to the start-up step and instituted prior to starting the compressor.

BW. The process of any one of Paragraphs BS-BV, wherein subsequent to including one or more of $H_2$ separated from the steam reformed product and/or the second reformed product, $H_2$ separated from the tail gas, or $H_2$ formed from subjecting at least a portion of the tail gas to the WGS reaction in the combustion gas, the inclusion of the steam reformed product and/or the second reformed product in the combustion gas is reduced, minimized, or discontinued.

BX. The process of any one of Paragraphs BS-BW, wherein subsequent to starting the compressor, inclusion of the steam reformed product and/or the second reformed product in the combustion gas is reduced, minimized, or discontinued.

BY. The process of any one of Paragraphs BS-BX, wherein
- a first start-up step occurs in a first reforming enclosure; and
- a second start-up step in a second reforming enclosure utilizes a portion of one or more of $H_2$ separated from the steam reformed product and/or the second reformed product, $H_2$ separated from the tail gas, or $H_2$ formed from subjecting at least a portion of the tail gas to the WGS reaction produced downstream of the first reforming enclosure.

BZ. The process of any one of Paragraphs BR-BY, further comprising a periodic synthesis catalyst regeneration step wherein the controlled flow communication is discontinued for the duration of the synthesis catalyst regeneration step.

CA. The process of Paragraph BZ, wherein the periodic synthesis catalyst regeneration step comprises
- a dewaxing step comprising flowing a dewaxing gas comprising $H_2$ over the synthesis catalyst;
- subsequent to the dewaxing step, an oxidation step comprising flowing an oxidation gas over the synthesis catalyst;
- subsequent to the oxidation step, a reduction step comprising exposing the synthesis catalyst to a reducing gas that comprises $H_2$.

CB. The process of Paragraph CA, wherein the dewaxing gas and/or the reducing gas comprises one or more of
- $H_2$ separated from the steam reformed product and/or the second reformed product,
- $H_2$ separated from the tail gas, or
- $H_2$ formed from subjecting at least a portion of the tail gas to the WGS reaction.

CC. The process of Paragraph CA or Paragraph CB, wherein the oxidation gas comprises the $O_2$-depleted gas or a portion thereof.

CD. The process of Paragraph CC, wherein the $O_2$-depleted gas or a portion thereof is used in the oxidation gas without substantial cooling.

CE. The process of any one of Paragraphs BR-CD, further comprising a periodic synthesis catalyst rejuvenation step wherein the controlled flow communication is discontinued for the duration of the synthesis catalyst rejuvenation step.

CF. The process of Paragraph CE, wherein the rejuvenation step comprises flowing a rejuvenation gas comprising $H_2$ over the synthesis catalyst.

CG. The process of Paragraph CF, wherein the rejuvenation gas may comprises one or more of
- $H_2$ separated from the steam reformed product and/or the second reformed product,
- $H_2$ separated from the tail gas, or
- $H_2$ formed from subjecting at least a portion of the tail gas to the WGS reaction.

CH. The process of any one of Paragraphs BZ-CG, further comprising the start-up step following the synthesis catalyst regeneration step or the synthesis catalyst rejuvenation step.

CI. A process comprising
forming ethylene by flowing a reactant feed comprising methane over a viral-templated coupling catalyst disposed on a permeate side of an ion transport membrane and
flowing an $O_2$-containing gas over a retentate side of the ion transport membrane; wherein
flowing the $O_2$-containing gas over the retentate side of the ion transport membrane produces an $O_2$-depleted gas.

CJ. The process of Paragraph CI, wherein the $O_2$-depleted gas is at a temperature of about 400° C. to about 1,000° C.

CK. The process of Paragraph CI or Paragraph CJ, wherein the flow of the reactant feed is co-current, counter-current, or cross-current to the flow of the $O_2$-containing gas.

CL. The process of any one of Paragraphs CI-CK, wherein the $O_2$-containing gas comprises air.

CM. The process of any one of Paragraphs CI-CL, wherein the $O_2$-depleted gas is about 0% to about 20.0% $O_2$.

CN. The process of any one of Paragraphs CI-CM, wherein the viral-templated coupling catalyst comprises at least one oxide of Cu, Pd, Ga, Sc, Y, Zr, In, Nd, Eu, Sm, Ce, Gd, Hf, Ho, Tm, W, La, Dy, In, S, Zn, Yb, Ni, Lu, Ta, P, Pt, Bi, Sn, Nb, Sb, Ge, Ag, Au, Pb, Re, Fe, Al, Tl, Pr, Co, Rh, Ti, V, Cr, Mn, Ir, As, Tb, Er, Te, Mo, or a combination of any two or more thereof as an oxide.

CO. The process of Paragraph CN, wherein the viral-templated coupling catalyst further comprises at least one alkali metal, alkali earth metal, or boron.

CP. The process of Paragraph CN or Paragraph CO, wherein the viral-templated coupling catalyst comprises a manganese oxide, an alkali metal, tungsten, and niobium, on a silica support.

CQ. The process of any one of Paragraphs CI-CP, wherein the viral-templated coupling catalyst is disposed on the surface of the ion transport membrane on the permeate side.

CR. The process of any one of Paragraphs CI-CQ, wherein forming ethylene is performed at a temperature of about 400° C. to about 1,000° C.

CS. The process of any one of Paragraphs CI-CR, wherein forming ethylene is performed at a temperature of about 400° C. to about 800° C.

CT. The process of any one of Paragraphs CI-CS, wherein the reactant feed is at a pressure falling in the range of about 1 atm to about 20 atm.

CU. The process of any one of Paragraphs CI-CT, wherein the partial pressure of methane in the reactant feed falls in the range of about 0.1 atm to about 20 atm.

CV. The process of any one of Paragraphs CI-CU, wherein the GSHV of the methane feed falls in the range of about 20,000 $hr^{-1}$ to about 5,000,000 $hr^{-1}$.

CW. The process of any one of Paragraphs CI-CV, wherein the process produces an ethylene formation product comprising ethylene.

CX. The process of Paragraph CW, wherein the ethylene formation product is separated to provide ethylene and an ethylene formation tail gas ("EF tail gas").

CY. The process of Paragraph CX, wherein the EF tail gas is directed to the pre-reformer or the WGS reaction of the process of any one of Paragraphs A-CH.

CZ. The process of any one of Paragraphs CI-CY, wherein forming ethylene provides heat to the steam reforming step of the process of any one of Paragraphs A-CH.

DA. The process of any one of Paragraphs CJ-CZ, further comprising contacting the ethylene with a synthesis catalyst to produce a synthetic product.

DB. The process of Paragraph DA, wherein the synthesis catalyst comprises an ethylene oxide production catalyst, a dimethoxyethane production catalyst, a vinyl acetate monomer production catalyst, or a combination of any two or more thereof.

Other embodiments are set forth in the following claims, along with the full scope of equivalents to which such claims are entitled.

What is claimed is:

1. A process comprising
steam reforming a first reforming feed to produce a steam reformed product comprising $H_2$ and CO ("the steam reforming step");
optionally subjecting a second reforming feed comprising the steam reformed product to a second reforming step to produce a second reformed product comprising $H_2$ and CO; and
contacting the $H_2$ and CO with a synthesis catalyst to produce a synthetic product and a tail gas ("the contacting step");
wherein
the synthetic product comprises one or more compounds selected from $C_1$ to $C_{100}$ hydrocarbons, $C_1$ to $C_{100}$ oxygenated hydrocarbons, or a combination thereof;
the first reforming feed comprises $CH_4$;
heat for the steam reforming step is provided by combustion and optionally partial oxidation;
the combustion and optional partial oxidation comprises flowing a combustion gas comprising $H_2$ over a permeate surface of an ion transport membrane and flowing an $O_2$-containing gas over a retentate surface of an ion transport membrane to react the combustion gas, produce heat, and produce an exhaust gas comprising $H_2O$ ("the combustion step"); and
the combustion gas comprises one or more of
$H_2$ separated from the steam reformed product and/or the second reformed product,
$H_2$ separated from the tail gas, or
$H_2$ formed from subjecting at least a portion of the tail gas to a water-gas shift ("WGS") reaction which forms a WGS product comprising $CO_2$ and $H_2$.

2. The process of claim 1, wherein at least the second reforming feed comprises one or more of
$H_2$ separated from the steam reformed product and/or the second reformed product, or
$H_2$ formed from subjecting at least a portion of the tail gas to the WGS reaction.

3. The process of claim 1, wherein the first reforming feed comprises the exhaust gas.

4. The process of claim 1, wherein the WGS reaction comprises a portion of $H_2O$ from the steam reformed product, a portion of $H_2O$ from the second reformed product, a portion of $H_2O$ produced in the contacting step, or a combination of any two or more thereof.

5. The process of claim 1, wherein the synthesis catalyst comprises a Fischer-Tropsch catalyst, a methanol production catalyst, a higher alcohol synthesis catalyst, or a combination of any two or more thereof.

6. The process of claim 1, wherein the initial mole ratio of $H_2$ to CO fed to the contacting step is in the range from about 0.5:1 to about 4:1.

7. The process of claim 1, wherein the contacting step comprises flowing the $H_2$ and CO through a microchannel reactor comprising the synthesis catalyst to produce the synthetic product.

8. A process comprising steam reforming a first reforming feed to produce a steam reformed product comprising $H_2$ and CO ("the steam reforming step");

optionally subjecting a second reforming feed comprising the steam reformed product to a second reforming step to produce a second reformed product comprising $H_2$ and CO; and contacting the $H_2$ and CO with a synthesis catalyst to produce a synthetic product and a tail gas ("the contacting step");

wherein
the synthetic product comprises one or more compounds selected from $C_1$ to $C_{100}$ hydrocarbons, $C_1$ to $C_{100}$ oxygenated hydrocarbons, or a combination thereof;
the first reforming feed comprises $CH_4$;
heat for the steam reforming step is provided by combustion and optionally partial oxidation;
the combustion and optional partial oxidation comprises flowing a combustion gas comprising $H_2$ over a permeate surface of an ion transport membrane and flowing an $O_2$-containing gas over a retentate surface of an ion transport membrane to react the combustion gas, produce heat, and produce an exhaust gas comprising $H_2O$ ("the combustion step"); and
the combustion gas comprises at least one or more of
$CO_2$ separated from the steam reformed product and/or the second reformed product,
$CO_2$ separated from the tail gas, or
$CO_2$ formed from subjecting at least a portion of the tail gas to a water-gas shift ("WGS") reaction which forms a WGS product comprising $CO_2$ and $H_2$.

9. The process of claim 8, wherein the first reforming feed comprises the exhaust gas.

10. The process of claim 8, wherein the process comprises subjecting the steam reformed product to the second reforming step to produce the second reformed product comprising $H_2$ and CO;

wherein the second reforming step comprises partial oxidation, autothermal reforming, $CO_2$ reforming, steam reforming, reverse water gas shift, or combinations of any two or more thereof.

11. The process of claim 8, wherein the contacting step comprises flowing the $H_2$ and CO through a microchannel reactor comprising the synthesis catalyst to produce the synthetic product.

12. The process of claim 8, wherein the synthesis catalyst comprises a Fischer-Tropsch catalyst, a methanol production catalyst, a higher alcohol synthesis catalyst, or a combination of any two or more thereof.

13. The process of claim 8, wherein the initial mole ratio of $H_2$ to CO fed to the contacting step is in the range from about 0.5:1 to about 4:1.

14. A process comprising steam reforming a first reforming feed to produce a steam reformed product comprising $H_2$ and CO ("the steam reforming step");

optionally subjecting a second reforming feed comprising the steam reformed product to a second reforming step to produce a second reformed product comprising $H_2$ and CO; and contacting the $H_2$ and CO with a synthesis catalyst to produce a synthetic product and a tail gas ("the contacting step");

wherein
the synthetic product comprises one or more compounds selected from $C_1$ to $C_{100}$ hydrocarbons, $C_1$ to $C_{100}$ oxygenated hydrocarbons, or a combination thereof;
the first reforming feed comprises $CH_4$;
heat for the steam reforming step is provided by combustion and optionally partial oxidation;
the combustion and optional partial oxidation comprises flowing a combustion gas comprising $H_2$ over a permeate surface of an ion transport membrane and flowing an $O_2$-containing gas over a retentate surface of an ion transport membrane to react the combustion gas, produce heat, and produce an exhaust gas comprising $H_2O$ ("the combustion step"); and
the combustion gas comprises one or more of
$H_2$ separated from the steam reformed product and/or the second reformed product,
$CO_2$ separated from the steam reformed product and/or the second reformed product,
$H_2$ separated from the tail gas,
$CO_2$ separated from the tail gas,
$H_2$ formed from subjecting at least a portion of the tail gas to a water-gas shift ("WGS") reaction which forms a WGS product comprising $CO_2$ and $H_2$, or
$CO_2$ formed from subjecting at least a portion of the tail gas to the WGS reaction.

15. The process of claim 14, wherein
the second reforming step is an autothermal reforming step comprising the combustion step,
the second reforming feed comprises the combustion gas,
an autothermal reforming ion transport membrane (ATR-ITM) comprises the ion transport membrane of the combustion step,
the second reformed product comprises the exhaust gas, and
the first reforming feed and second reforming feed do not comprise the exhaust gas.

16. The process of claim 15, wherein the autothermal reforming comprises flowing the second reforming feed over a permeate surface of the ATR-ITM and flowing the $O_2$-containing gas over a retentate surface of the ATR-ITM to produce the second reformed product.

17. The process of claim 14, wherein the WGS reaction comprises a portion of $H_2O$ from the steam reformed product, a portion of $H_2O$ from the second reformed product, a portion of $H_2O$ produced in the contacting step, or a combination of any two or more thereof.

18. The process of claim 14, comprising including a portion of the WGS product in the first reforming feed, the second reforming feed, or both.

19. The process of claim 14, wherein the contacting step comprises flowing the $H_2$ and CO through a microchannel reactor comprising the synthesis catalyst to produce the synthetic product.

20. The process of claim 14, the second reforming feed comprises the exhaust gas.

* * * * *